United States Patent
Nath et al.

(10) Patent No.: US 12,226,416 B2
(45) Date of Patent: Feb. 18, 2025

(54) METHODS AND MATERIALS FOR IMPROVING ARTERIOVENOUS FISTULA MATURATION AND MAINTAINING ARTERIOVENOUS FISTULA FUNCTIONALITY

(71) Applicant: Mayo Foundation for Medical Education and Research, Rochester, MN (US)

(72) Inventors: Karl A. Nath, Rochester, MN (US); James L. Kirkland, Rochester, MN (US); Tamar Tchkonia, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 18/432,824

(22) Filed: Feb. 5, 2024

(65) Prior Publication Data

US 2024/0238289 A1   Jul. 18, 2024

Related U.S. Application Data

(62) Division of application No. 16/973,723, filed as application No. PCT/US2019/038569 on Jun. 21, 2019, now Pat. No. 11,925,640.

(60) Provisional application No. 62/688,822, filed on Jun. 22, 2018.

(51) Int. Cl.
*A61K 31/506* (2006.01)
*A61K 31/355* (2006.01)
*A61P 9/10* (2006.01)

(52) U.S. Cl.
CPC .......... *A61K 31/506* (2013.01); *A61K 31/355* (2013.01); *A61P 9/10* (2018.01)

(58) Field of Classification Search
CPC .. A61K 31/506; A61K 31/355; A61K 31/352; A61P 9/10; A61P 13/12
See application file for complete search history.

(56) References Cited

U.S. PATENT DOCUMENTS

| | | | |
|---|---|---|---|
| 6,632,789 | B1 | 10/2003 | June |
| 11,925,640 | B2 | 3/2024 | Nath et al. |
| 2004/0009949 | A1 | 1/2004 | Krieg |
| 2007/0178605 | A1 | 8/2007 | Mor et al. |
| 2010/0160314 | A1 | 6/2010 | Lipford et al. |
| 2010/0210596 | A1 | 8/2010 | Bluestone et al. |
| 2010/0318016 | A1* | 12/2010 | Nugent ............... A61M 1/00 604/8 |
| 2015/0133390 | A1 | 5/2015 | Khatri et al. |
| 2017/0198253 | A1 | 7/2017 | Laberge et al. |
| 2017/0216286 | A1 | 8/2017 | Kirkland et al. |
| 2017/0360732 | A1 | 12/2017 | Tumlin |
| 2021/0244734 | A1 | 8/2021 | Nath et al. |
| 2021/0283185 | A1 | 9/2021 | Kirkland et al. |
| 2021/0379068 | A1 | 12/2021 | Kirkland et al. |

FOREIGN PATENT DOCUMENTS

| | | |
|---|---|---|
| DE | 102008031036 | 12/2009 |
| WO | WO 2006/108035 | 10/2006 |
| WO | WO 2006/109300 | 10/2006 |
| WO | WO 2013/035099 | 3/2013 |
| WO | WO 2005/031364 | 4/2015 |
| WO | WO 2015/116735 | 8/2015 |
| WO | WO 2015/116740 | 8/2015 |
| WO | WO 2016/127135 | 8/2016 |

OTHER PUBLICATIONS

Acosta et al., "A complex secretory program orchestrated by the inflammasome controls paracrine senescence," Nat. Cell Biology, Jun. 16, 2013, 15(8):978-990.
Adams et al., "Second-Order Pyramidal Slip in Zinc Single Crystals," Mater. Sci. Engineering, Nov. 1967, 2(4):201-207.
Adhikari et al., "Basomedial amygdala mediates top-down control of anxiety and fear," Nature, Nov. 4, 2015, 527(7577):179-185.
Al-Khalidi et al., "Insights on the Robust Variance Estimator under Recurrent-Events Model," Biometrics, Mar. 18, 2011, 67(4):1564-1572.
Ambrosi et al., "Adipocyte Accumulation in the Bone Marrow during Obesity and Aging Impairs Stem Cell-Based Hematopoietic and Bone Regeneration," Cell Stem Cell, Mar. 16, 2017, 20(6):771-784.e6.
Anacker et al., "Adult hippocampal neurogenesis and cognitive flexibility—linking memory and mood," Nat. Rev. Neuroscience, May 4, 2017, 18(6):335-346.
Ananth et al., "Pre-eclampsia rates in the United States, 1980-2010: age-period-cohort analysis," BMJ, Nov. 7, 2013, 347:f6564, 2 pages.
Awaya et al., "Telomere Shortening in Hematopoietic Stem Cell Transplantation: A Potential Mechanism for Late Graft Failure?," Biol. Blood Marrow Transplant, 2002, 8(11):597-600.
Ayala et al., "Standard operating procedures for describing and performing metabolic tests of glucose homeostasis in mice," Dis. Model. Mechanisms, Aug. 16, 2010, 3(9-10):525-534.
Baar et al., "Targeted Apoptosis of Senescent Cells Restores Tissue Homeostasis in Response to Chemotoxicity and Aging," Cell, Mar. 23, 2017, 169(1):132-147.e16.
Baker et al., "Clearance of p16Ink4a-positive senescent cells delays ageing-associated disorders," Nature, Nov. 2, 2011, 479(7372):232-236.

(Continued)

*Primary Examiner* — Alicia L Otton
*Assistant Examiner* — David M Shim
(74) *Attorney, Agent, or Firm* — Fish & Richardson P.C.

(57) ABSTRACT

This document provides methods and materials for improving arteriovenous fistula (AVF) maturation and/or maintaining AVF functionality. For example, methods and materials for using one or more senolytic agents to improve AVF maturation, to maintain AVF functionality, and/or to maintain the patency of an AVF are provided. Methods and materials for using one or more senolytic agents to maintain functionality and/or patency of a venous graft (e.g., a venous graft that bypasses an occluded artery) also are provided.

16 Claims, 13 Drawing Sheets

(56) References Cited

OTHER PUBLICATIONS

Baker et al., "Naturally occurring p16Ink4a-positive cells shorten healthy lifespan," Nature, Feb. 3, 2016, 530(7589):184-189.
Benjamin et al., "Heart Disease and Stroke Statistics—2017 Update: A Report From the American Heart Association," Circulation, Jan. 25, 2017, 135(10):e146-e603.
Berry et al., "Cellular Aging Contributes to Failure of Cold-Induced Beige Adipocyte Formation in Old Mice and Humans," Cell Metabolism, Nov. 23, 2016, 25(1):166-181.
Beyer et al., "Inflammation-related muscle weakness and fatigue in geriatric patients," Exp. Gerontology, Jan. 2012, 47(1):52-59.
Bibbins-Domingo et al., "Screening for Preeclampsia: US Preventive Services Task Force Recommendation Statement," JAMA, Apr. 25, 2017, 317(16):1661-1667.
Bitto et al., "Transient rapamycin treatment can increase lifespan and healthspan in middle-aged mice," Elife, Aug. 23, 2016, 5:e16351, 17 pages.
Blande et al., "Adipose tissue mesenchymal stem cell expansion in animal serum-free medium supplemented with autologous human platelet lysate," Transfusion, Aug. 18, 2009, 49(12):2680-2685.
Brack et al., "Increased Wnt Signaling During Aging Alters Muscle Stem Cell Fate and Increases Fibrosis," Science, Aug. 10, 2007, 317(5839):807-810.
Brenner et al., "A standard of fetal growth for the United States of America," Am. J. Obstet. Gynecology, Nov. 1, 1976, 126(5):555-564.
Bushnell et al., "Guidelines for the Prevention of Stroke in Women: A Statement for Healthcare Professionals From the American Heart Association/American Stroke Association," Stroke, Feb. 6, 2014, 45(5):1545-1588.
Bussian et al., "Clearance of senescent glial cells prevents tau-dependent pathology and cognitive decline," Nature, Sep. 19, 2018, 562(7728):578-582.
Caballero, "Endothelial dysfunction in obesity and insulin resistance: A road to diabetes and heart disease," Obes. Research, Nov. 2003, 11(11):1278-1289.
Campisi et al., "Cellular senescence: when bad things happen to good cells," Nat. Rev. Mol. Cell Biology, Sep. 2007, 8(9):729-740.
Canetti et al., "Deterioration of mental health in bariatric surgery after 10 years despite successful weight loss," Eur. J. Clin. Nutrition, Jul. 22, 2015, 70(1):17-22.
Capelli et al., "Human platelet lysate allows expansion and clinical grade production of mesenchymal stromal cells from small samples of bone marrow aspirates or marrow filter washouts," Bone Marrow Transplantation, Aug. 6, 2007, 40(8):785-791.
Capuron et al., "Immune system to brain signaling: neuropsychopharmacological implications," Pharmacol. Therapeutics, May 2011, 130(2):226-238.
Carlson et al., "Muscle transplantation between young and old rats: age of host determines recovery," Am. J. Physiology, Jun. 1989, 256(6):C1262-C1266.
Carroll et al., "Total and High-density Lipoprotein Cholesterol in Adults: United States, 2015-2016," NCHS Data Brief, Oct. 2017, (290):1-8.
Castellano et al., "Human umbilical cord plasma proteins revitalize hippocampal function in aged mice," Nature, Apr. 19, 2017, 544(7651):488-492.
Castrechini et al., "Mesenchymal stem cells in human placental chorionic villi reside in a vascular Niche," Placenta, Jan. 13, 2010, 31(3):203-212.
CDC.gov [online], "National Diabetes Statistics Report, 2017: Estimates of Diabetes and its Burden in the United States," Available on or before Jun. 27, 2018 via Internet Archive: Wayback Machine URL<https://web.archive.org/web/20180627072719/https://www.cdc.gov/diabetes/pdfs/data/statistics/national-diabetes-statistics-report.pdf>, retrieved on Jun. 21, 2021, 20 pages.
Chade et al., "Endothelial Progenitor Cells Homing and Renal Repair in Experimental Renovascular Disease," Stem Cells, Jun. 2010, 28(6):1039-1047.
Chade et al., "Endothelial Progenitor Cells Restore Renal Function in Chronic Experimental Renovascular Disease," Circulation, Jan. 19, 2009, 119(4):547-557.
Chang et al., "Clearance of senescent cells by ABT263 rejuvenates aged hematopoietic stem cells in mice," Nat. Medicine, Dec. 14, 2015, 22(1):78-83.
Chang et al., "Statins Improve Long Term Patency of Arteriovenous Fistula for Hemodialysis," Sci. Reports, Feb. 23, 2016, 6:22197, 10 pages.
Chen et al., "Ablation of XP-V gene causes adipose tissue senescence and metabolic abnormalities," Proc. Nat. Acad. Sci. USA, Aug. 3, 2015, 112(33):E4556-E4564.
Chen et al., "Trafficking of Multipotent Mesenchymal Stromal Cells from Maternal Circulation through the Placenta Involves Vascular Endothelial Growth Factor Receptor-1 and Integrins," Stem Cells, Feb. 2008, 26(2):550-561.
Childs et al., "Senescent intimal foam cells are deleterious at all stages of atherosclerosis," Science, Oct. 27, 2016, 354(6311):472-477.
Chinta et al., "Cellular Senescence Is Induced by the Environmental Neurotoxin Paraquat and Contributes to Neuropathology Linked to Parkinson's Disease," Cell Reports, Jan. 23, 2018, 22(4):930-940.
Choi et al., "Neurorestorative role of stem cells in Alzheimer's disease: astrocyte involvement," Curr. Alzheimer Research, Mar. 1, 2016, 13(4):419-427.
Christopher et al., "Metabolism and disposition of dasatinib after oral administration to humans," Drug Metab. Disposition, Apr. 17, 2008, 36(7):1357-1364.
Cignarelli et al., "Human adipose tissue stem cells: relevance in the pathophysiology of obesity and metabolic diseases and therapeutic applications," Expert Rev. Mol. Medicine, Dec. 10, 2012, 14:e19, 21 pages.
Cohen et al., "The Association of Plasma IL-6 Levels With Functional Disability in Community-Dwelling Elderly," J. Gerontol. A Biol. Sci. Med. Sciences, Jul. 1997, 52(4):M201-208.
Cohen et al., "The Medical Expenditure Panel Survey: A National Information Resource to Support Healthcare Cost Research and Inform Policy and Practice," Med. Care, Jul. 2009, 47(7 Suppl 1):S44-S50.
Collard et al., "Prevalence of Frailty in Community-Dwelling Older Persons: A Systematic Review," J. Am. Geriatr. Society, Aug. 6, 2012, 60(8):1487-1492.
Conboy et al., "Rejuvenation of aged progenitor cells by exposure to a young systemic environment," Nature, Feb. 17, 2005, 433(7027):760-764.
Coppé et al., "Senescence-Associated Secretory Phenotypes Reveal Cell-Nonautonomous Functions of Oncogenic RAS and the p53 Tumor Suppressor," PLoS Biology, Dec. 2, 2008, 6(12):2853-2868.
Correia-Melo et al., "Mitochondria are required for pro-ageing features of the senescent phenotype," EMBO Journal, Feb. 4, 2016, 35(7):724-742.
Costa et al., "Mechanisms of Neuroprotection by Quercetin: Counteracting Oxidative Stress and More," Oxid. Med. Cell Longevity, Jan. 24, 2016, 2016:2986796, 11 pages.
Cox et al., "The role of cellular senescence in ageing of the placenta," Placenta, Jan. 16, 2017, 52:139-145.
Crimmins, "Lifespan and Healthspan: Past, Present, and Promise," Gerontologist, Nov. 10, 2015, 55(6):901-911.
Croatt et al., "Characterization of a Model of an Arteriovenous Fistula in the Rat: The Effect of L-NAME," Am. J. Pathology, Apr. 2, 2010, 176(5):2530-2541.
Croy et al., "Reduced Olfactory Bulb Volume in Adults with a History of Childhood Maltreatment," Chem. Senses, Oct. 2013, 38(8):679-684.
Cui et al., "Combined use of serum MCP-1/IL-10 ratio and uterine artery Doppler index significantly improves the prediction of preeclampsia," Clin. Chim. Acta, Dec. 27, 2016, 473:228-236.
Cunningham et al., "Investigation of Antidepressant Medication Usage after Bariatric Surgery," Obes. Surgery, Sep. 8, 2011, 22(4):530-535.
Cupit-Link et al., "Biology of premature ageing in survivors of cancer," ESMO Open, Dec. 18, 2017, 2(5):e000250, 8 pages.

(56) References Cited

OTHER PUBLICATIONS

D'Adda di Fagagna et al., "A DNA damage checkpoint response in telomere-initiated senescence," Nature, Nov. 5, 2003, 426(6963):194-198.
Da Silva Meirelles et al., "Mesenchymal stem cells reside in virtually all post-natal organs and tissues," J. Cell Science, Jun. 2006, 119(Pt 11):2204-2213.
Daghini et al., "Antioxidant vitamins induce angiogenesis in the normal pig kidney," Am. J. Physiol. Renal Physiology, Apr. 11, 2007, 293(1):F371-F381.
Demaria et al., "An Essential Role for Senescent Cells in Optimal Wound Healing through Secretion of PDGF-AA," Dev. Cell, Dec. 11, 2014, 31(6):722-733.
Demaria et al., "Cellular Senescence Promotes Adverse Effects of Chemotherapy and Cancer Relapse," Cancer Discovery, Dec. 15, 2016, 7(2):165-176.
Dimri et al., "A biomarker that identifies senescent human cells in culture and in aging skin in vivo," Proc. Natl. Acad. Sci. USA, Sep. 26, 1995, 92(20):9363-9367.
Dinel et al., "Cognitive and Emotional Alterations Are Related to Hippocampal Inflammation in a Mouse Model of Metabolic Syndrome," PLoS One, Sep. 16, 2011, 6(9):e24325, 10 pages.
Dou et al., "Cytoplasmic chromatin triggers inflammation in senescence and cancer," Nature, Oct. 4, 2017, 550(7676):402-406.
Drew et al., "Modulation of Aversive Memory by Adult Hippocampal Neurogenesis," Neurotherapeutics, May 9, 2017, 14(3):646-661.
Egerman et al., "GDF11 Increases with Age and Inhibits Skeletal Muscle Regeneration," Cell Metabolism, May 19, 2015, 22(1):164-174.
Eirin et al., "Adipose tissue-derived mesenchymal stem cells improve revascularization outcomes to restore renal function in swine atherosclerotic renal artery stenosis," Stem Cells, May 2012, 30(5):1030-1041.
Eirin et al., "Endothelial Outgrowth Cells Shift Macrophage Phenotype and Improve Kidney Viability in Swine Renal Artery Stenosis," Arterioscler. Thromb. Vasc. Biology, Feb. 21, 2013, 33(5):1006-1013.
EP Search Report in European Appln. No. 19821748.1, dated Aug. 2, 2021, 4 pages.
Fabbri et al., "Aging and Multimorbidity: New Tasks, Priorities, and Frontiers for Integrated Gerontological and Clinical Research," J. Am. Med. Dir. Association, May 7, 2015, 16(8):640-647.
Farmer, "Transcriptional control of adipocyte formation," Cell Metabolism, Oct. 2006, 4(4):263-273.
Farr et al., "Identification of Senescent Cells in the Bone Microenvironment," J. Bone Miner. Research, Oct. 24, 2016, 31(11):1920-1929.
Farr et al., "Targeting cellular senescence prevents age-related bone loss in mice," Nat. Medicine, Aug. 21, 2017, 23(9):1072-1079.
Fisher et al., "Mental Illness in Bariatric Surgery: A Cohort Study from the Portal Network," Obesity, May 2017, 25(5):850-856.
Flowers et al., "Comparative analysis of risk factors for acute graft-versus-host disease and for chronic graft-versus-host disease according to National Institutes of Health consensus criteria," Blood, Jan. 24, 2011, 117(11):3214-3219.
Fogt et al., "Recipient-Derived Hepatocytes in Liver Transplants: A Rare Event in Sex-Mismatched Transplants," Hepatology, Jul. 2002, 36(1):173-176.
Franceschi et al., "Inflammaging and 'Garb-aging'," Trends Endocrinol. Metabolism, Oct. 24, 2016, 28(3):199-212.
Frasca et al., "Aging, obesity, and inflammatory age-related diseases," Front. Immunology, Dec. 7, 2017, 8:1745, 10 pages.
Fried et al., "Frailty in older adults: evidence for a phenotype," J. Gerontol. A Biol. Sci. Med. Sciences, Mar. 2001, 56(3):M146-156.
Friedman et al., "Biochemical Corroboration of Endothelial Involvement in Severe Preeclampsia," Am. J. Obstet. Gynecology, Jan. 1995, 172(1 Pt 1):202-203.
Friend et al., "Basal Ganglia Dysfunction Contributes to Physical Inactivity in Obesity," Cell Metabolism, Dec. 29, 2016, 25(2):312-321.
Fries, "Aging, Natural Death, and the Compression of Morbidity," N. Engl. J. Medicine, Jul. 17, 1980, 303(3):130-135.
Fuhrmann-Stroissnigg et al., "Identification of HSP90 inhibitors as a novel class of senolytics," Nat. Communications, Sep. 4, 2017, 8(1):422, 14 pages.
Gao et al., "Crosstalk of metabolic factors and neurogenic signaling in adult neurogenesis: implication of metabolic regulation for mental and neurological diseases," Neurochem. International, Jun. 2017, 106:24-36.
Gariepy et al., "The association between obesity and anxiety disorders in the population: a systematic review and meta-analysis," Int. J. Obesity, Dec. 8, 2009, 34(3):407-419.
Garovic et al., "Carotid Artery Intima-Media Thickness and Subclinical Atherosclerosis in Women With Remote Histories of Preeclampsia: Results From a Rochester Epidemiology Project-Based Study and Meta-analysis," Mayo Clin. Proceedings, Aug. 25, 2017, 92(9):1328-1340.
Garovic et al., "Hypertension in pregnancy as a risk factor for cardiovascular disease later in life," J. Hypertension, Apr. 2010, 28(4):826-833.
Garovic et al., "Hypertension in pregnancy: an emerging risk factor for cardiovascular disease," Nat. Clin. Pract. Nephrology, Nov. 2007, 3(11):613-622.
Garovic et al., "Incidence and Long-Term Outcomes of Hypertensive Disorders of Pregnancy," J. Am. Coll. Cardiology, May 12, 2020, 75(18):2323-2334.
Geller et al., "International Classification of Diseases—9th revision coding for preeclampsia: how accurate is it?," Am. J. Obstet. Gynecology, Jun. 2004, 190(6):1629-1633.
GenBank Accession No. NM_001165413.2, "*Homo sapiens* serpin peptidase inhibitor, clade E (nexin, plasminogen activator inhibitor type 1), member 1 (SERPINE1), transcript variant 2, mRNA," dated Mar. 10, 2013, 4 pages.
GenBank Accession No. NM_001318095.1, "*Homo sapiens* interleukin 6 (IL6), transcript variant 2, mRNA," dated Jun. 16, 2017, 3 pages.
GenBank Accession No. NM_002982.3, "*Homo sapiensb*C-C motif chemokine ligand 2 (CCL2), mRNA," dated Jun. 11, 2017, 4 pages.
Giessing et al., "Outcomes of transplanting deceased-donor kidneys between elderly donors and recipients," J. Am. Soc. Nephrology, Dec. 10, 2008, 20(1):37-40.
Glinka et al., "Olfactory Deficits Cause Anxiety-Like Behaviors in Mice," J. Neuroscience, May 9, 2012, 32(19):6718-6725.
Gnecchi et al., "Paracrine Mechanisms in Adult Stem Cell Signaling and Therapy," Circ. Research, Nov. 21, 2008, 103(11):1204-1219.
Goodman et al., "Defining and measuring chronic conditions: imperatives for research, policy, program, and practice," Prev. Chronic Disease, Apr. 25, 2013, 10:E66, 16 pages.
Graefe et al., "Pharmacokinetics and bioavailability of quercetin glycosides in humans," J. Clin. Pharmacology, May 2001, 41(5):492-499.
Grant et al., "Adult hematopoietic stem cells provide functional hemangioblast activity during retinal neovascularization," Nat. Medicine, Jun. 2002, 8(6):607-612.
Greer et al., "Increased concentrations of cytokines interleukin-6 and interleukin-1 receptor antagonist in plasma of women with preeclampsia: a mechanism for endothelial dysfunction?," Obstet. Gynecology, Dec. 1994, 84(6):937-940.
Guidi et al., "Osteopontin attenuates aging-associated phenotypes of hematopoietic stem cells," EMBO Journal, Mar. 2, 2017, 36(7):840-853.
Guillemot-Legris et al., "Obesity-Induced Neuroinflammation: Beyond the Hypothalamus," Trends Neurosciences, Apr. 2017, 40(4):237-253.
Guo et al., "WT1 is a key regulator of podocyte function: Reduced expression levels cause crescentic glomerulonephritis and mesangial sclerosis," Hum. Mol. Genetics, Mar. 15, 2002, 11(6):651-659.
Gussoni et al., "Dystrophin expression in the mdx mouse restored by stem cell transplantation," Nature, Sep. 23, 1999, 401(6751):390-394.
Gustafson et al., "Insulin resistance and impaired adipogenesis," Trends Endocrinol. Metabolism, Feb. 18, 2015, 26(4):193-200.

(56) References Cited

OTHER PUBLICATIONS

Hall et al., "Aging of mice is associated with p16(Ink4a)- and β-galactosidase-positive macrophage accumulation that can be induced in young mice by senescent cells," Aging, Jul. 2016, 8(7):1294-1315.
Hall et al., "p16(Ink4a) and senescence-associated beta-galactosidase can be induced in macrophages as part of a reversible response to physiological stimuli," Aging, Aug. 2, 2017, 9(8):1867-1884.
Hamilton et al., "Aberrant Lipid Metabolism in the Forebrain Niche Suppresses Adult Neural Stem Cell Proliferation in an Animal Model of Alzheimer's Disease," Cell Stem Cell, Oct. 1, 2015, 17(4):397-411.
Hamm et al., "Role of PPARγ in regulating adipocyte differentiation and insulin-responsive glucose uptake," Ann. NY Acad. Sciences, Nov. 18, 1999, 892:134-145.
Hasan et al., "Skin capillary density changes in normal pregnancy and pre-eclampsia," J. Hypertension, Dec. 2002, 20(12):2439-2443.
Hazra et al., "Experimental reduction of miR-92a mimics arterial aging," Exp. Gerontology, Oct. 2016, 83:165-170.
Helman et al., "p16Ink4a-induced senescence of pancreatic beta cells enhances insulin secretion," Nat. Medicine, Mar. 7, 2016, 22(4):412-420.
Hewitt et al., "Telomeres are favoured targets of a persistent DNA damage response in ageing and stress-induced senescence," Nat. Communications, Feb. 28, 2012, 3:708, 9 pages.
Heyward et al., "Adult mice maintained on a high-fat diet exhibit object location memory deficits and reduced hippocampal SIRT1 gene expression," Neurobiol. Learn. Memory, Jul. 2012, 98(1):25-32.
Hodgson et al., "What determines ageing of the transplanted liver?," HPB (Oxford), Sep. 28, 2014, 17(3):222-225.
Honigberg et al., "Long-Term Cardiovascular Risk in Women With Hypertension During Pregnancy," J. Am. Coll. Cardiology, Nov. 11, 2019, 74(22):2743-2754.
Howe et al., "RNA-Seq analysis in MeV," Bioinformatics, Oct. 5, 2011, 27(22):3209-3210.
Hůrza et al., "Effect of Parabiosis of Young and Old Rats on Aortic Calcification and Collagen Cross-Links," Exp. Gerontology, Dec. 1967, 2(4):201-207.
Hryhorczuk et al., "Metabolic disturbances connecting obesity and depression," Front. Neuroscience, Oct. 7, 2013, 7:177.
Idilman et al., "Recipient-Derived Hepatocytes in Sex-Mismatched Liver Allografts after Liver Transplantation: Early versus Late Transplant Biopsies," Transplantation, Dec. 15, 2004, 78(11):1647-1652.
Ikeno et al., "Housing Density Does Not Influence the Longevity Effect of Calorie Restriction," J. Gerontol. A Biol. Sci. Med. Sciences, Dec. 2005, 60(12):1510-1517.
International Society of Nephrology, "KDIGO Clinical Practice Guideline for the Diagnosis, Evaluation, Prevention, and Treatment of Chronic Kidney Disease-Mineral and Bone Disorder (CKD-MBD)," Kidney International, Aug. 2009, 76(S113):S1-S130.
Ivanov et al., "Lysosome-mediated processing of chromatin in senescence," J. Cell Biology, Jul. 1, 2013, 202(1):129-143.
Jackson et al., "Regeneration of ischemic cardiac muscle and vascular endothelium by adult stem cells," J. Clin. Investigation, Jun. 2001, 107(11):1395-1402.
Jackson, "Multi-state models for panel data: The msm package for R," J. Stat. Software, Jan. 4, 2011, 38(8):1-28.
James et al., "Can we fix it? Evaluating the potential of placental stem cells for the treatment of pregnancy disorders," Placenta, Dec. 30, 2013, 35(2):77-84.
Jeon et al., "Local clearance of senescent cells attenuates the development of post-traumatic osteoarthritis and creates a pro-regenerative environment," Nat. Medicine, Apr. 24, 2017, 23(6):775-781.
Juncos et al., "Genetic deficiency of heme oxygenase-1 impairs functionality and form of an arteriovenous fistula in the mouse," Kidney International, Jul. 1, 2008, 74(1):47-51.

Juncos et al., "MCP-1 Contributes to Arteriovenous Fistula Failure," J. Am. Soc. Nephrology, Jan. 2011, 22(1):43-48.
Jurk et al., "Chronic inflammation induces telomere dysfunction and accelerates ageing in mice," Nat. Communications, Jun. 24, 2014, 2:4172, 14 pages.
Jurk et al., "Postmitotic neurons develop a p21-dependent senescence-like phenotype driven by a DNA damage response," Aging Cell, Aug. 9, 2012, 11(6):996-1004.
Justice et al., "Cellular senescence biomarker p16INK4a+ cell burden in thigh adipose is associated with poor physical function in older women," J. Gerontol. A Biol. Sci. Med. Sciences, Jun. 27, 2017, 73(7):939-945.
Justice et al., "Frameworks for Proof-of-Concept Clinical Trials of Interventions That Target Fundamental Aging Processes," J. Gerontol. A Biol. Sci. Med. Sciences, Aug. 16, 2016, 71(11):1415-1423.
Justice et al., "Senolytics in idiopathic pulmonary fibrosis: Results from a first-in-human, open-label, pilot study," EBioMedicine, Feb. 1, 2019, 40:554-563.
Kadowaki et al., "Adiponectin and adiponectin receptors in insulin resistance, diabetes, and the metabolic syndrome," J. Clin. Investigation, Jul. 2006, 116(7):1784-1792.
Kahn et al., "Obesity and insulin resistance," J. Clin. Investigation, Aug. 2000, 106(4):473-481.
Kalantar et al., "Serum levels of tumor necrosis factor-α, interleukin-15 and interleukin-10 in patients with pre-eclampsia in comparison with normotensive pregnant women," Iran J. Nurs. Midwifery Res., Nov. 2013, 18(6):463-466.
Kalari et al., "MAP-RSeq: Mayo Analysis Pipeline for RNA sequencing," BMC Bioinformatics, Jun. 27, 2014, 15:224, 11 pages.
Kalinderis et al., "Elevated Serum Levels of Interleukin-6, Interleukin-1β and Human Chorionic Gonadotropin in Pre-eclampsia," Am. J. Reprod. Immunol., May 2011, 66(6):468-475.
Kane et al., "Animal models of frailty: current applications in clinical research," Clin. Interv. Aging, Oct. 26, 2016, 11:1519-1529.
Kang et al., "A new model of an arteriovenous fistula in chronic kidney disease in the mouse: beneficial effects of upregulated heme oxygenase-1," Am. J. Physiol. Renal Physiology, Dec. 16, 2015, 310(6):F466-F476.
Kang et al., "Induction and functional significance of the heme oxygenase system in pathological shear stress in vivo," Am. J. Physiol. Heart Circ. Physiology, Mar. 27, 2015, 308(11):H1402-H1413.
Kang et al., "The DNA damage response induces inflammation and senescence by inhibiting autophagy of GATA4," Science, Sep. 25, 2015, 349(6255):aaa5612.
Kao et al., "Examining how p16(INK4a) expression levels are linked to handgrip strength in the elderly," Sci. Reports, Aug. 23, 2016, 6:31905, 5 pages.
Katsimpardi et al., "Vascular and Neurogenic Rejuvenation of the Aging Mouse Brain by Young Systemic Factors," Science, May 5, 2014, 344(6184):630-634.
Kattah et al., "Preeclampsia and ESRD: The Role of Shared Risk Factors," Am. J. Kidney Disease, Oct. 1, 2016, 69(4):498-505.
Kennedy et al., "The Mechanistic Target of Rapamycin: The Grand ConducTOR of Metabolism and Aging," Cell Metabolism, Jun. 14, 2016, 23(6):990-1003.
Kirkland et al., "Cellular Senescence: A Translational Perspective," EBioMedicine, Apr. 12, 2017, 21:21-28.
Kirkland et al., "Clinical strategies and animal models for developing senolytic agents," Exp. Gerontology, Oct. 28, 2014, 68:19-25.
Kirkland et al., "The Clinical Potential of Senolytic Drugs," J. Am. Geriatr. Society, Sep. 4, 2017, 65(10):2297-2301.
Klemmensen et al., "Validity of Preeclampsia-related Diagnoses Recorded in a National Hospital Registry and in a Postpartum Interview of the Women," Am. J. Epidemiology, Jun. 7, 2007, 166(2):117-124.
Klungsøyr et al., "Validity of Pre-Eclampsia Registration in the Medical Birth Registry of Norway for Women Participating in the Norwegian Mother and Child Cohort Study, 1999-2010," Paediatr. Perinat. Epidemiology, Jul. 18, 2014, 28(5):362-371.
Kollman et al., "Donor characteristics as risk factors in recipients after transplantation of bone marrow from unrelated donors: the effect of donor age," Blood, Oct. 1, 2001, 98(7):2043-2051.

(56) References Cited

OTHER PUBLICATIONS

Kørbling et al., "Adult Stem Cells for Tissue Repair—A New Therapeutic Concept?," N. Engl. J. Medicine, Aug. 7, 2003, 349(6):570-582.

Kørbling et al., "Hepatocytes and epithelial cells of donor origin in recipients of peripheral-blood stem cells," N. Engl. J. Medicine, Mar. 7, 2002, 346(10):738-746.

Kouidrat et al., "Surgical Management of Obesity Among People with Schizophrenia and Bipolar Disorder: a Systematic Review of Outcomes and Recommendations for Future Research," Obes. Surgery, May 15, 2017, 27(7):1889-1895.

Krause et al., "Multi-Organ, Multi-Lineage Engraftment by a Single Bone Marrow-Derived Stem Cell," Cell, May 4, 2001, 105(3):369-377.

Krishnamoorthy et al., "Anatomic configuration affects the flow rate and diameter of porcine arteriovenous fistulae," Kidney International, Apr. 2, 2012, 81(8):745-750.

Krtolica et al., "Cancer and aging: a model for the cancer promoting effects of the aging stroma," Int. J. Biochem. Cell Biology, Nov. 2002, 34(11):1401-1414.

Krtolica et al., "GROα regulates human embryonic stem cell self-renewal or adoption of a neuronal fate," Differentiation, Apr. 2011, 81(4):222-232.

Kueckelhaus et al., "Transformation of Face Transplants: Volumetric and Morphologic Graft Changes Resemble Aging After Facial Allotransplantation," Am. J. Transplantation, Dec. 7, 2015, 16(3):968-978.

Kuklina et al., "Hypertensive Disorders and Severe Obstetric Morbidity in the United States," Obstet. Gynecology, Jun. 2009, 113(6):1299-1306.

Kusumbe et al., "Age-dependent modulation of vascular niches for haematopoietic stem cells," Nature, Apr. 13, 2016, 532(7599):380-384.

Laberge et al., "MTOR regulates the pro-tumorigenic senescence-associated secretory phenotype by promoting IL1A translation," Nat. Cell Biology, Jul. 6, 2015, 17(8):1049-1061.

Lagasse et al., "Purified hematopoietic stem cells can differentiate into hepatocytes in vivo," Nat. Medicine, Nov. 2000, 6(11):1229-1234.

Lasselin et al., "Chronic Low-Grade Inflammation in Metabolic Disorders: Relevance for Behavioral Symptoms," Neuroimmunomodulation, Feb. 14, 2014, 21(2-3):95-101.

Latham et al., "Human Blood and Cardiac Stem Cells Synergize to Enhance Cardiac Repair When Cotransplanted Into Ischemic Myocardium," Circulation, Sep. 10, 2013, 128(11 Suppl 1):S105-S112.

Lau et al., "Mixing old and young: enhancing rejuvenation and accelerating aging," J. Clin. Investigation, Jan. 2, 2019, 129(1):4-11.

Lawler et al., "Population-Based Analysis of Hypertensive Disorders in Pregnancy," Hypertens. Pregnancy, 2007, 26(1):67-76.

Levine et al., "Trial of calcium to prevent preeclampsia," N. Engl. J. Medicine, Jul. 10, 1997, 337(2):69-76.

Li et al., "Control of obesity and glucose intolerance via building neural stem cells in the hypothalamus," Mol. Metabolism, Jun. 2014, 3(3):313-324.

Liang et al., "Effects of aging on the homing and engraftment of murine hematopoietic stem and progenitor cells, " Blood, Apr. 12, 2005, 106(4):1479-1487.

Lisonkova et al., "Incidence of preeclampsia: risk factors and outcomes associated with early-versus late-onset disease," Am. J. Obstet. Gynecology, Aug. 22, 2013, 209(6):544.e1-544.e12.

Liu et al., "Augmented Wnt Signaling in a Mammalian Model of Accelerated Aging," Science, Aug. 10, 2007, 317(5839):803-806.

Locke et al., "Diagnosis and Management of Generalized Anxiety Disorder and Panic Disorder in Adults," Am. Fam. Physician, May 1, 2015, 91(9):617-624.

Loffredo et al., "Growth Differentiation Factor 11 Is a Circulating Factor that Reverses Age-Related Cardiac Hypertrophy," Cell, May 9, 2013, 153(4):828-839.

Lok et al., "Cumulative patency of contemporary fistulas versus grafts (2000-2010)," Clin. J. Am. Soc. Nephrology, May 7, 2013, 8(5):810-818.

Londero et al., "Placental aging and oxidation damage in a tissue micro-array model: an immunohistochemistry study," Histochem. Cell Biology, Apr. 22, 2016, 146(2):191-204.

Lu et al., "Inflammatory and immune markers associated with physical frailty syndrome: findings from Singapore longitudinal aging studies," Oncotarget, May 17, 2016, 7(20):28783-28795.

Luo et al., "Single-cell transcriptome analyses reveal signals to activate dormant neural stem cells," Cell, May 21, 2015, 161(5):1175-1186.

Lykouras et al., "Anxiety disorders and obesity," Psychiatriki, Oct. 2011, 22(4):307-313.

Malaquin et al., "Keeping the senescence secretome under control: Molecular reins on the senescence-associated secretory phenotype," Exp. Gerontology, May 25, 2016, 82:39-49.

Maryanovich et al., "Adrenergic nerve degeneration in bone marrow drives aging of the hematopoietic stem cell niche," Nat. Medicine, May 7, 2018, 24(6):782-791.

Mason et al., "Transplantation of Young Ovaries to Old Mice Increased Life Span in Transplant Recipients," J. Gerontol. A Biol. Sci. Med. Sciences, Sep. 23, 2009, 64(12):1207-1211.

Matini et al., "The comparison of severity and prevalence of major depressive disorder, general anxiety disorder and eating disorders before and after bariatric surgery," Med. J. Islam Repub. Iran, Oct. 8, 2014, 28:109, 7 pages.

Matsushita et al., "Mesenchymal stem cells in obesity: insights for translational applications," Lab. Investigation, Apr. 17, 2007, 97(10):1158-1166.

Mehrotra et al., "Vascular Access for Hemodialysis and Value-Based Purchasing for ESRD," J. Am. Soc. Nephrology, Feb. 2017, 28(2):395-397.

Mehta et al., "Does younger donor age affect the outcome of reduced-intensity allogeneic hematopoietic stem cell transplantation for hematologic malignancies beneficially?," Bone Marrow Transplantation, Jun. 5, 2006, 38(2):95-100.

Michaud et al., "Proinflammatory cytokines, aging, and age-related diseases," J. Am. Med. Dir. Association, Dec. 1, 2013, 14(12):877-882.

Michos et al., "Framingham risk equation underestimates subclinical atherosclerosis risk in asymptomatic women," Atherosclerosis, Jan. 2006, 184(1):201-206.

Milic et al., "Electronic Algorithm Is Superior to Hospital Discharge Codes for Diagnoses of Hypertensive Disorders of Pregnancy in Historical Cohorts," Mayo Clin. Proceedings, Dec. 2018, 93(12):1707-1719.

Milic et al., "Preclinical atherosclerosis at the time of pre-eclamptic pregnancy and up to 10 years postpartum: systematic review and meta-analysis," Ultrasound Obstet. Gynecology, Jan. 2017, 49(1):110-115.

Miller et al., "An Aging Interventions Testing Program: study design and interim report," Aging Cell, Jun. 18, 2007, 6(4):565-575.

Min et al., "Dendritic Cells Genetically Engineered to Express Fas Ligand Induce Donor-Specific Hyporesponsiveness and Prolong Allograft Survival," J. Immunology, Jan. 1, 2000, 164(1):161-167.

Minami et al., "Senolytic Drug Treatment Attenuates mtDNA-Mediated Inflammatory Injury in Old Donors and Prolongs Cardiac Allograft Survival," Presented at Proceedings of the 2018 American Transplant Congress, Seattle, WA, Jun. 2-6, 2018, Abstract No. 99, 4 pages.

Minamino et al., "A crucial role for adipose tissue p53 in the regulation of insulin resistance," Nat. Medicine, Aug. 30, 2009, 15(9):1082-1087.

Mirotsou et al., "Secreted frizzled related protein 2 (Sfrp2) is the key Akt-mesenchymal stem cell-released paracrine factor mediating myocardial survival and repair," Proc. Natl. Acad. Sci. USA, Jan. 30, 2007, 104(5): 1643-1648.

Mitterberger et al., "Adipogenic Differentiation Is Impaired in Replicative Senescent Human Subcutaneous Adipose-Derived Stromal/Progenitor Cells," J. Gerontol. A Biol. Sci. Med. Sciences, May 8, 2013, 69(1):13-24.

(56) References Cited

OTHER PUBLICATIONS

Mizunoya et al., "Effect of dietary fat type on anxiety-like and depression-like behavior in mice," Springerplus, Apr. 16, 2013, 2(1):165, 9 pages.

Moncsek et al., "Targeting senescent cholangiocytes and activated fibroblasts with B-cell lymphoma-extra large inhibitors ameliorates fibrosis in multidrug resistance 2 gene knockout (Mdr2-/-) mice," Hepatology, Nov. 29, 2017, 67(1):247-259.

Mongraw-Chaffin et al., "Preeclampsia and Cardiovascular Disease Death: Prospective Evidence From the Child Health and Development Studies Cohort," Hypertension, Jun. 1, 2010, 56(1):166-171.

Montani et al., "Pulmonary Arterial Hypertension in Patients Treated by Dasatinib," Circulation, Mar. 26, 2012, 125(17):2128-2137.

Mosca et al., "Effectiveness-Based Guidelines for the Prevention of Cardiovascular Disease in Women—2011 Update," Circulation, Mar. 22, 2011, 123(11):1243-1262.

Mosca et al., "Effectiveness-Based Guidelines for the Prevention of Cardiovascular Disease in Women—2011 Update," J. Am. Coll. Cardiology, Mar. 22, 2011, 57(12):1404-1423.

Mosca et al., "Guide to Preventive Cardiology for Women," Circulation, May 11, 1999, 99(18):2480-2484.

Mosier et al., "Homozygous scid/scid;beige/beige mice have low levels of spontaneous or neonatal T cell-induced B cell generation," J. Exp. Medicine, Jan. 1993, 177(1):191-194.

Munoz et al., "Human stem/progenitor cells from bone marrow promote neurogenesis of endogenous neural stem cells in the hippocampus of mice," Proc. Natl. Acad. Sci. USA, Dec. 13, 2005, 102(50):18171-18176.

Munoz-Espin et al., "Cellular senescence: from physiology to pathology," Nat. Rev. Mol. Cell Biology, Jun. 23, 2014, 15(7):482-496.

Musi et al., "Tau protein aggregation is associated with cellular senescence in the brain," Aging Cell, Oct. 11, 2018, 17(6):e12840.

Nademanee et al., "The outcome of matched unrelated donor bone marrow transplantation in patients with hematologic malignancies using molecular typing for donor selection and graft-versus-host disease prophylaxis regimen of cyclosporine, methotrexate, and prednisone," Blood, Aug. 1, 1995, 86(3):1228-1234.

Naito et al., "Complement C1q Activates Canonical Wnt Signaling and Promotes Aging-Related Phenotypes," Cell, Jun. 8, 2012, 149(6):1298-1313.

Nakabayashi et al., "Elevated IL-6 in midtrimester amniotic fluid is involved with the onset of preeclampsia," Am. J. Reprod. Immunol., May 1998, 39(5):329-334.

Nama et al., "Structural capillary rarefaction and the onset of preeclampsia," Obstet. Gynecology, May 2012, 119(5):967-974.

Narita et al., "Rb-Mediated Heterochromatin Formation and Silencing of E2F Target Genes during Cellular Senescence," Cell, Jun. 13, 2003, 113(6):703-716.

Nath et al., "Challenges in Developing New Therapies for Vascular Access Dysfunction," Clin. J. Am. Soc. Nephrology, Dec. 2017, 12(12):2053-2055.

Nath et al., "Increased Venous Proinflammatory Gene Expression and Intimal Hyperplasia in an Aorto-Caval Vistula Model in the Rat," Am. J. Pathology, Jun. 2003, 162(6):2079-2090.

Nath et al., "Predicting the Functionality and Form of a Dialysis Fistula," J. Am. Soc. Nephrology, Dec. 2016, 27(12):3508-3510.

Nath et al., "The murine dialysis fistula model exhibits a senescence phenotype: pathobiological mechanisms and therapeutic potential," Am. J. Physiol. Renal Physiology, Jul. 16, 2018, 315(5):F1493-F1499.

National High Blood Pressure Education Program Working Group on High Blood Pressure in Pregnancy, "Report of the National High Blood Pressure Education Program Working Group on High Blood Pressure in Pregnancy," Am. J. Obstet Gynecology, Jul. 2000, 183(1):S1-S22.

Negoias et al., "Reduced olfactory bulb volume and olfactory sensitivity in patients with acute major depression," Neuroscience, May 13, 2010, 169(1):415-421.

Nelson et al., "A senescent cell bystander effect: senescence-induced senescence," Aging Cell, Feb. 9, 2012, 11(2):345-349.

Ness et al., "Frailty in childhood cancer survivors," Cancer, Dec. 19, 2014, 121(10):1540-1547.

Niemann et al., "Correspondence: Therapeutic Hypothermia in Deceased Organ Donors and Kidney-Graft Function," N. Engl. J. Medicine, Dec. 31, 2015, 373(27):2686-2687.

Niemann et al., "Therapeutic Hypothermia in Deceased Organ Donors and Kidney-Graft Function," N. Engl. J. Medicine, Jul. 30, 2015, 373(5):405-414.

Nowak et al., "IL-9 as a mediator of Th17-driven inflammatory disease," J. Exp. Medicine, Jul. 13, 2009, 206(8):1653-1660.

Nunemaker et al., "Increased serum CXCL1 and CXCLS are linked to obesity, hyperglycemia, and impaired islet function," J. Endocrinology, Jun. 13, 2014, 222(2):267-276.

Oberhuber et al., "CD11c+ Dendritic Cells Accelerate the Rejection of Older Cardiac Transplants via Interleukin-17A," Circulation, May 8, 2015, 132(2):122-131.

Ogrodnik et al., "Cellular senescence drives age-dependent hepatic steatosis," Nat. Communications, Jun. 13, 2017, 8:15691, 12 pages.

Ogrodnik et al., "Integrating cellular senescence with the concept of damage accumulation in aging: Relevance for clearance of senescent cells," Aging Cell, Oct. 22, 2018, 18(1):e12841.

Ogrodnik et al., "Obesity-Induced Cellular Senescence Drives Anxiety and Impairs Neurogenesis," Cell Metabolism, Jan. 3, 2019, 29(5):1061-1077.e8.

Okuma et al., "p16Ink4a and p21Cip1/Waf1 promote tumour growth by enhancing myeloid-derived suppressor cells chemotaxis," Nat. Communications, Dec. 12, 2017, 8(1):2050, 13 pages.

Olefsky et al., "Macrophages, Inflammation, and Insulin Resistance," Annu. Rev. Physiology, Mar. 2010, 72:219-246.

Olivieri et al., "MicroRNAs linking inflamm-aging, cellular senescence and cancer," Ageing Res. Reviews, Sep. 2013, 12(4):1056-1068.

Orlic et al., "Bone marrow cells regenerate infarcted myocardium," Nature, Apr. 5, 2001, 410(6829):701-705.

Osborn et al, "G protein-coupled receptor 21 deletion improves insulin sensitivity in diet-induced obese mice," J. Clin. Investigations, Jun. 1, 2012, 122(7):2444-2453.

Ota et al., "Induction of endothelial nitric oxide synthase, SIRT1, and catalase by statins inhibits endothelial senescence through the Akt pathway," Arterioscler Thromb Vasc Biol, Nov. 2010, 30(11):2205-2211.

Ożarowski et al., "Pharmacological Effect of Quercetin in Hypertension and Its Potential Application in Pregnancy-Induced Hypertension: Review of In Vitro, In Vivo, and Clinical Studies," Evid Based Complement Alternat Medicine, Dec. 2, 2018, 2018:7421489, 19 pages.

Pajvani et al., "Fat apoptosis through targeted activation of caspase 8: a new mouse model of inducible and reversible lipoatrophy," Nat. Medicine, Jun. 19, 2005, 11(7):797-803.

Palmer et al., "Aging and adipose tissue: potential interventions for diabetes and regenerative medicine," Exp. Gerontology, Feb. 26, 2016, 86:97-105.

Palmer et al., "Cellular Senescence in Type 2 Diabetes: A Therapeutic Opportunity," Diabetes, Jul. 2015, 64(7):2289-2298.

Palmer et al., "Targeting senescent cells alleviates obesity-induced metabolic dysfunction," Aging Cell, Mar. 25, 2019, 18(3):e12950.

Passos et al., "Feedback between p21 and reactive oxygen production is necessary for cell senescence," Mol. Syst. Biology, Feb. 16, 2010, 6:347, 14 pages.

PCT International Preliminary Report on Patentability in International Appln. No. PCT/US2019/038569, dated Dec. 22, 2020, 7 pages.

PCT International Search Report and Written Opinion in International Appln. No. PCT/US2019/038569, dated Sep. 30, 2019, 9 pages.

Peterson et al., "Improved survival of mesenchymal stromal cell after hypoxia preconditioning: Role of oxidative stress," Life Sciences, Jan. 3, 2011, 88(1-2):65-73.

Potente et al., "Vascular heterogeneity and specialization in development and disease," Nat. Rev. Mol. Cell Biology, May 24, 2017, 18(8):477-494.

(56) References Cited

OTHER PUBLICATIONS

Poulos et al., "Endothelial transplantation rejuvenates aged hematopoietic stem cell function," J. Clin. Investigation, Oct. 16, 2017, 127(11):4163-4178.
Pricola et al., "Interleukin-6 Maintains Bone Marrow-Derived Mesenchymal Stem Cell Stemness by an ERK1/2-Dependent Mechanism," J. Cell. Biochemistry, Oct. 15, 2009, 108(3):577-588.
Psychiatry.org [online], "Clinical Practice Guidelines," available on or before Aug. 22, 2015 via Internet Archive: Wayback Machine URL<https://web.archive.org/web/20150822191558/psychiatry.org/psychiatrists/practice/clinical-practice-guidelines>, retrieved on Jun. 17, 2021, retrieved from URL<psychiatry.org/psychiatrists/practice/clinical-practice-guidelines>, 5 pages.
Ranganath et al., "Harnessing the Mesenchymal Stem Cell Secretome for the Treatment of Cardiovascular Disease," Cell Stem Cell, Mar. 2, 2012, 10(3):244-258.
Remuzzi et al., "Long-Term Outcome of Renal Transplantation from Older Donors," N. Engl. J. Medicine, Jan. 26, 2006. 354(4):343-352.
Reuben et al., "The Associations Between Physical Activity and Inflammatory Markers in High-Functioning Older Persons: MacArthur Studies of Successful Aging," J. Am. Geriatr. Society, Jul. 31, 2003, 51(8):1125-1130.
Riella et al., "Vascular access in haemodialysis: strengthening the Achilles' heel," Nat. Rev. Nephrology, Apr. 16, 2013, 9(6):348-357.
Ritschka et al., "The senescence-associated secretory phenotype induces cellular plasticity and tissue regeneration," Genes Development, Jan. 31, 2017, 31(2):172-183.
Roberts et al., "Hypertension in Pregnancy: Report of the American College of Obstetricians and Gynecologists' Task Force on Hypertension in Pregnancy," Obstet. Gynecology, Nov. 2013, 122(5):1122-1131.
Robinson et al., "edgeR: a Bioconductor package for differential expression analysis of digital gene expression data," Bioinformatics, Nov. 11, 2009, 26(1):139-140.
Rocca et al., "Accelerated Accumulation of Multimorbidity After Bilateral Oophorectomy: A Population-Based Cohort Study," Mayo Clin. Proceedings, Sep. 29, 2016, 91(11):1577-1589.
Rocca et al., "Prevalence of Multimorbidity in a Geographically Defined American Population: Patterns by Age, Sex, and Race/Ethnicity," Mayo Clin. Proceedings, Sep. 11, 2014, 89(10):1336-1349.
Rolfo et al., "Pro-inflammatory profile of preeclamptic placental mesenchymal stromal cells: new insights into the etiopathogenesis of preeclampsia, " PloS One, Mar. 2013, 8(3):e59403, 13 pages.
Roos et al., "Chronic senolytic treatment alleviates established vasomotor dysfunction in aged or atherosclerotic mice," Aging Cell, Feb. 10, 2016, 15(5):973-977.
Roy-Chaudhury et al., "Hemodialysis Vascular Access Dysfunction: A Cellular and Molecular Viewpoint," J. Am. Soc. Nephrology, Apr. 2006, 17(4):1112-1127.
Rudra et al., "Monthly variation in preeclampsia prevalence: Washington State, 1987-2001," J. Matern. Fetal Neonatal Medicine, Nov. 2005, 18(5):319-324.
Ryan et al., "Mesenchymal stem cells avoid allogeneic rejection," J. Inflammation, Jul. 26, 2005, 2:8, 11 pages.
Saad et al., "Adipose-derived mesenchymal stem cells from patients with atherosclerotic renovascular disease have increased DNA damage and reduced angiogenesis that can be modified by hypoxia," Stem Cell Res. Therapy, Sep. 9, 2016, 7(1):128, 12 pages.
Saad et al., "Autologous Mesenchymal Stem Cells Increase Cortical Perfusion in Renovascular Disease," J. Am. Soc. Nephrology, May 1, 2017, 28(9):2777-2785.
Saftlas et al., "Epidemiology of preeclampsia and eclampsia in the United States, 1979-1986," Am. J. Obstet. Gynecology, Aug. 1990, 163(2):460-465.
Saha et al., "A comparison of some approximate confidence intervals for a single proportion for clustered binary outcome data," Int. J. Biostatistics, Nov. 1, 2016, 12(2):20150024, 18 pages.
Salazar Garcia et al., "Early pregnancy immune biomarkers in peripheral blood may predict preeclampsia," J. Reprod. Immunology, Feb. 2018, 125:25-31.
Sanada et al., "Source of Chronic Inflammation in Aging," Front. Cardiovasc. Medicine, Feb. 22, 2018, 5:12, 5 pages.
Sata et al., "Hematopoietic stem cells differentiate into vascular cells that participate in the pathogenesis of atherosclerosis," Nat. Medicine, Apr. 1, 2002, 8(4):403-409.
Schafer et al., "Cellular senescence mediates fibrotic pulmonary disease," Nat. Communications, Feb. 23, 2017, 8:14532, 11 pages.
Schafer et al., "Exercise Prevents Diet-Induced Cellular Senescence in Adipose Tissue," Diabetes, Mar. 16, 2016, 65(6):1606-1615.
Schafer et al., "Quantification of GDF11 and Myostatin in Human Aging and Cardiovascular Disease," Cell Metabolism, Jun. 14, 2016, 23(6):1207-1215.
Schwerfeld-Bohr et al., "Influence of Hematopoietic Stem Cell-Derived Hepatocytes on Liver Regeneration after Sex-Mismatched Liver Transplantation in Humans," J. Invest. Surgery, May 9, 2012, 25(4):220-226.
Shen et al., "Transplantation of mesenchymal stem cells from young donors delays aging in mice," Sci. Reports, Aug. 18, 2011, 1:67, 7 pages.
Shimabukuro et al., "Lipid-laden cells differentially distributed in the aging brain are functionally active and correspond to distinct phenotypes," Sci. Reports, Mar. 31, 2016, 6:23795, 12 pages.
Shohara et al., "Mesenchymal stromal cells of human umbilical cord Wharton's jelly accelerate wound healing by paracrine mechanisms," Cytotherapy, Sep. 1, 2012, 14(10):1171-1181.
Sidorenko et al., "Functional rearrangement of lymphohemopoietic system in heterochronically parabiosed mice," Mech. Ageing Development, Sep. 1986, 36(1):41-56.
Simon et al., "Thigmotaxis as an index of anxiety in mice. Influence of dopaminergic transmissions," Behav. Brain Research, Mar. 31, 1994, 61(1):59-64.
Sinha et al., "Restoring systemic GDF11 levels reverses age-related dysfunction in mouse skeletal muscle," Science, May 5, 2014, 344(6184):649-652.
Siopi et al., "Anxiety- and Depression-Like States Lead to Pronounced Olfactory Deficits and Impaired Adult Neurogenesis in Mice," J. Neuroscience, Jan. 13, 2016, 36(2):518-531.
Smith et al., "β2-microglobulin is a systemic pro-aging factor that impairs cognitive function and neurogenesis," Nat. Medicine, Jul. 6, 2015, 21(8):932-937.
Song et al., "Prevalence and 10-year outcomes of frailty in older adults in relation to deficit accumulation," J. Am. Geriatr. Society, Apr. 1, 2010, 58(4):681-687.
Srinivas-Shankar et al., "Frailty and muscle function: role for testosterone?," Front. Horm. Research, 2009, 37:133-149.
St. Sauver et al., "Data Resource Profile: The Rochester Epidemiology Project (REP) medical records-linkage system," Int. J. Epidemiology, Dec. 2012, 41(6):1614-1624.
St. Sauver et al., "Use of a Medical Records Linkage System to Enumerate a Dynamic Population Over Time: The Rochester Epidemiology Project," Am. J. Epidemiology, Mar. 23, 2011, 173(9):1059-1068.
Stern et al., "Adiponectin, Leptin, and Fatty Acids in the Maintenance of Metabolic Homeostasis through Adipose Tissue Crosstalk," Cell Metabolism, May 10, 2016, 23(5):770-784.
Stunkard et al., "Psychological aspects of severe obesity," Am. J. Clin. Nutrition, Feb. 1992, 55(2):524S-532S.
Suvakov et al., "Targeting senescence improves angiogenic potential of adipose-derived mesenchymal stem cells in patients with preeclampsia," Biol. Sex Differences, Sep. 14, 2019, 10(1):49, 13 pages.
Takasugi et al., "Small extracellular vesicles secreted from senescent cells promote cancer cell proliferation through EphA2," Nat. Communications, Jun. 6, 2017, 8:15729, 11 pages.
Takasugi, "Emerging roles of extracellular vesicles in cellular senescence and aging," Aging Cell, Feb. 1, 2018, 17(2):e12734.
Tardelli et al., "Osteopontin is a key player for local adipose tissue macrophage proliferation in obesity," Mol. Metabolism, Sep. 13, 2016, 5(11):1131-1137.

(56) References Cited

OTHER PUBLICATIONS

Tchkonia et al., "Abundance of two human preadipocyte subtypes with distinct capacities for replication, adipogenesis, and apoptosis varies among fat depots," Am. J. Physiol. Endocrinol. Metabolism, Sep. 21, 2004, 288(1):E267-E277.

Tchkonia et al., "Cellular senescence and the senescent secretory phenotype: therapeutic opportunities," J. Clin. Investigation, Mar. 1, 2013, 123(3):966-972.

Tchkonia et al., "Fat tissue, aging, and cellular senescence," Aging Cell, Sep. 16, 2010, 9(5):667-684.

Tchkonia et al., "Increased TNFα and CCAAT/enhancer-binding protein homologous protein with aging predispose preadipocytes to resist adipogenesis," Am. J. Physiol. Endocrinol. Metabolism, Oct. 2, 2007, 293(6):E1810-E1819.

Tchkonia et al., "Mechanisms and Metabolic Implications of Regional Differences among Fat Depots," Cell Metabolism, Apr. 11, 2013, 17(5):644-656.

Tesch, "Role of macrophages in complications of type 2 diabetes," Clin. Exp. Pharmacol. Physiology, Oct. 2007, 34(10):1016-1019.

Toma et al., "Human Mesenchymal Stem Cells Differentiate to a Cardiomyocyte Phenotype in the Adult Murine Heart," Circulation, Jan. 1, 2002, 105(1):93-98.

Tompkins et al., "Allogeneic Mesenchymal Stem Cells Ameliorate Aging Frailty: A Phase II Randomized, Double-Blind, Placebo-Controlled Clinical Trial," J. Gerontol. A Biol. Sci. Med. Sciences, Oct. 12, 2017, 72(11):1513-1522.

Towfighi et al., "A midlife stroke surge among women in the United States," Neurology, Nov. 13, 2007, 69(20):1898-1904.

Towfighi et al., "Sex-Specific Trends in Midlife Coronary Heart Disease Risk and Prevalence," Arch. Intern. Medicine, Oct. 26, 2009, 169(19):1762-1766.

Tran et al., "Beneficial Effects of Subcutaneous Fat Transplantation on Metabolism," Cell Metabolism, May 2008, 7(5):410-420.

Uchida et al., "Bile Acid Metabolism in Young-Old Parabiotic Rats," Lipids, Apr. 1997, 32(4):383-390.

Ulrich-Lai et al., "Neuroendocrine Circuits Governing Energy Balance and Stress Regulation: Functional Overlap and Therapeutic Implications," Cell Metabolism, Jun. 3, 2014, 19(6):910-925.

Vader et al., "Extracellular vesicles: emerging targets for cancer therapy," Trends Mol. Medicine, Apr. 3, 2014, 20(7):385-393.

Van Deursen, "The role of senescent cells in ageing," Nature, May 22, 2014, 509(7501):439-446.

Van Raemdonck et al., "Ex-vivo lung perfusion," Transpl. International, Mar. 15, 2014, 28(6):643-656.

Vas et al., "Aging of the Microenvironment Influences Clonality in Hematopoiesis," PLoS One, Aug. 6, 2012, 7(8):e42080, 6 pages.

Vas et al., "Contribution of an Aged Microenvironment to Aging-Associated Myeloproliferative Disease," PLoS One, Feb. 21, 2012, 7(2):e31523, 9 pages.

Viecelli et al., "The pathogenesis of hemodialysis vascular access failure and systemic therapies for its prevention: Optimism unfulfilled," Semin. Dialysis, Nov. 26, 2017, 31(3):244-257.

Villeda et al., "The ageing systemic milieu negatively regulates neurogenesis and cognitive function," Nature, Aug. 31, 2011, 477(7362):90-94.

Villeda et al., "Young blood reverses age-related impairments in cognitive function and synaptic plasticity in mice," Nat. Medicine, May 4, 2014, 20(6):659-663.

Wagner et al., "Extreme obesity is associated with suicidal behavior and suicide attempts in adults: results of a population-based representative sample," Depress. Anxiety, Apr. 10, 2013, 30(10):975-981.

Wallis et al., "Secular Trends in the Rates of Preeclampsia, Eclampsia, and Gestational Hypertension, United States, 1987-2004," Am. J. Hypertension, May 2008, 21(5):521-526.

Walston et al., "The Physical and Biological Characterization of a Frail Mouse Model," J. Gerontol. A Biol. Sci. Med. Sciences, Apr. 2008, 63(4):391-398.

Wang et al., "Albumin-expressing hepatocyte-like cells develop in the livers of immune-deficient mice that received transplants of highly purified human hematopoietic stem cells," Blood, Jan. 30, 2003, 101(10):4201-4208.

Wang et al., "Cardiomyopathy and Worsened Ischemic Heart Failure in SM22-alpha Cre-Mediated Neuropilin-1 Null Mice: Dysregulation of PGC1alpha and Mitochondrial Homeostasis," Arterioscler. Thromb. Vasc. Biology, Jun. 2015, 35(6):1401-1412.

Wang et al., "DNA damage response and cellular senescence in tissues of aging mice," Aging Cell, May 26, 2009, 8(3):311-323.

Wang et al., "Leptin- and Leptin Receptor-Deficient Rodent Models: Relevance for Human Type 2 Diabetes," Curr. Diabetes Reviews, Mar. 2014, 10(2):131-145.

Wang et al., "RSeQC: quality control of RNA-seq experiments," Bioinformatics, Jun. 27, 2012, 28(16):2184-2185.

Wang et al., "Total body irradiation selectively induces murine hematopoietic stem cell senescence," Blood, Sep. 8, 2005, 107(1):358-366.

Webster et al., "Target of Rapamycin Inhibitors (Sirolimus and Everolimus) for Primary Immunosuppression of Kidney Transplant Recipients: A Systematic Review and Meta-Analysis of Randomized Trials," Transplantation, May 15, 2006, 81(9):1234-1248.

Weilner et al., "Vesicular Galectin-3 levels decrease with donor age and contribute to the reduced osteo-inductive potential of human plasma derived extracellular vesicles," Aging, Jan. 2016, 8(1):16-33.

Weisberg et al., "Obesity is associated with macrophage accumulation in adipose tissue," J. Clin. Investigation, Dec. 2003, 112(12):1796-1808.

Weissgerber et al., "From Static to Interactive: Transforming Data Visualization to Improve Transparency," PLoS Biology, Jun. 22, 2016, 4(6):e1002484, 8 pages.

Weissgerber et al., "Hypertension in Pregnancy and Future Cardiovascular Event Risk in Siblings," J. Am. Soc. Nephrology, Mar. 2016, 27(3):894-902.

Weissgerber et al., "Impaired Flow-Mediated Dilation Before, During, and After Preeclampsia: A Systematic Review and Meta-Analysis," Hypertension, Feb. 2016, 67(2):415-423.

Weissgerber et al., "Preeclampsia and Diabetes," Curr. Diab. Reports, Feb. 3, 2015, 15(3):9, 10 pages.

Weissgerber et al., "Uric Acid: A Missing Link Between Hypertensive Pregnancy Disorders and Future Cardiovascular Disease?," Mayo Clin. Proceedings, Sep. 2015, 90(9):1207-1216.

Wiley et al., "From Ancient Pathways to Aging Cells—Connecting Metabolism and Cellular Senescence," Cell Metabolism, Jun. 14, 2016, 23(6):1013-1021.

Wiley et al., "Mitochondrial Dysfunction Induces Senescence with a Distinct Secretory Phenotype," Cell Metabolism, Feb. 9, 2016, 23(2):303-314.

Wilson et al., "Navitoclax, a targeted high-affinity inhibitor of BCL-2, in lymphoid malignancies: A phase 1 dose-escalation study of safety, pharmacokinetics, pharmacodynamics, and antitumour activity," Lancet Oncology, Dec. 2010, 11(12):1149-1159.

World Health Organization [online], "Obesity and overweight," available on or before Apr. 25, 2018 via Internet Archive: Wayback Machine URL<https://web.archive.org/web/20180425031715/https://www.who.int/news-room/fact-sheets/detail/obesity-and-overweight>, retrieved on Jun. 17, 2021, retrieved from URL<https://www.who.int/news-room/fact-sheets/detail/obesity-and-overweight>, 6 pages.

Xu et al., "JAK inhibition alleviates the cellular senescence-associated secretory phenotype and frailty in old age," Proc. Natl. Acad. Sci. USA, Nov. 2, 2015, 112(46):E6301-E6310.

Xu et al., "Perspective: Targeting the JAK/STAT pathway to fight age-related dysfunction," Pharmacol. Research, Sep. 2016, 111:152-154.

Xu et al., "Senolytics improve physical function and increase lifespan in old age," Nat. Medicine, Jul. 9, 2018, 24(8):1246-1256.

Xu et al., "Targeting senescent cells enhances adipogenesis and metabolic function in old age," Elife, Dec. 19, 2015, 4:e12997, 19 pages.

(56) References Cited

OTHER PUBLICATIONS

Xu et al., "Transplanted Senescent Cells Induce an Osteoarthritis-Like Condition in Mice," J. Gerontol. A Biol. Sci. Med. Sciences, Jun. 1, 2017, 72(6):780-785.

Xu, "Preparation, culture, and immortalization of mouse embryonic fibroblasts," Curr. Protoc. Mol. Biology, May 2005, 28:28.1.1-28.1.8.

Xue, "The Frailty Syndrome: Definition and Natural History," Clin. Geriatr. Medicine, Feb. 2011, 27(1): 1-15.

Yahata et al., "Accumulation of oxidative DNA damage restricts the self-renewal capacity of human hematopoietic stem cells," Blood, Jul. 6, 2011, 118(11):2941-2950.

Yang et al., "Ameliorative effects of pre-eclampsia by quercetin supplement to aspirin in a rat model induced by L-NAME," Biomed. Pharmacotherapy, May 16, 2019, 116:108969, 6 pages.

Yosef et al., "Directed elimination of senescent cells by inhibition of BCL-W and BCL-XL," Nat. Communications, Apr. 6, 2016, 7:11190, 11 pages.

Yoshimoto et al., "Obesity-induced gut microbial metabolite promotes liver cancer through senescence secretome," Nature, Jun. 26, 2013, 499(7456):97-101.

Young et al., "The influence of host and tissue age on life span and growth rate of serially transplanted mouse mammary gland," Exp. Gerontology, Feb. 1, 1971, 6(1):49-56.

Yousefzadeh et al., "Fisetin is a senotherapeutic that extends health and lifespan," EBioMedicine, Sep. 29, 2018, 36:18-28.

Zaragosi et al., "Activin A Plays a Critical Role in Proliferation and Differentiation of Human Adipose Progenitors," Diabetes, Jun. 8, 2010, 59(10):2513-2521.

Zhang et al., "Severe maternal morbidity associated with hypertensive disorders in pregnancy in the United States," Hypertens. Pregnancy, 2003, 22(2):203-212.

Zhao et al., "Differential expression of microRNAs in decidua-derived mesenchymal stem cells from patients with pre-eclampsia," J. Biomed. Science, Aug. 19, 2014, 21(1):81, 12 pages.

Zhu et al., "Cellular senescence and the senescent secretory phenotype in age-related chronic diseases," Curr. Opin. Clin. Nutr. Metab. Care, Jul. 2014, 17(4):324-328.

Zhu et al., "Disparate effects of simvastatin on angiogenesis during hypoxia and inflammation," Life Sciences, Dec. 5, 2008, 83(23-24):801-809.

Zhu et al., "Enhanced endothelial progenitor cell angiogenic potency, present in early experimental renovascular hypertension, deteriorates with disease duration," J. Hypertension, Oct. 2011, 29(10):1972-1979.

Zhu et al., "Identification of a novel senolytic agent, navitoclax, targeting the Bcl-2 family of anti-apoptotic factors," Aging Cell, Mar. 18, 2016, 15(3):428-435.

Zhu et al., "Mesenchymal stem cells and endothelial progenitor cells decrease renal injury in experimental swine renal artery stenosis through different mechanisms," Stem Cells, Jan. 2013, 31(1):117-125.

Zhu et al., "New agents that target senescent cells: the flavone, fisetin, and the BCL-XL inhibitors, A1331852 and A1155463," Aging, Mar. Mar. 8, 2017, 9(3):955-963.

Zhu et al., "The Achilles' heel of senescent cells: from transcriptome to senolytic drugs," Aging Cell, Mar. 9, 2015, 14(4):644-658.

Zuniga et al., "IL-17 regulates adipogenesis, glucose homeostasis, and obesity," J. Immunology, Oct. 29, 2010, 185(11):6947-6959.

U.S. Appl. No. 17/257,923, filed Jan. 5, 2021, James L. Kirkland, Published as U.S. Publication No. 2021/0283185.

U.S. Appl. No. 17/288,258, filed Apr. 23, 2021, James L. Kirkland, Published as U.S. Publication No. 2021/0379068.

U.S. Appl. No. 17/632,958, filed Feb. 4, 2022, Vesna D. Garovic, Published as U.S. Publication No. 2024/0016804.

U.S. Appl. No. 17/977,654, filed Oct. 31, 2022, James L. Kirkland, Published as U.S. Publication No. 2023/0218617.

\* cited by examiner

Sham

AVF-CKD

METHODS AND MATERIALS FOR IMPROVING ARTERIOVENOUS FISTULA MATURATION AND MAINTAINING ARTERIOVENOUS FISTULA FUNCTIONALITY

CROSS-REFERENCE TO RELATED APPLICATIONS

This application is a divisional of U.S. application Ser. No. 16/973,723, filed Dec. 9, 2020, which is a National Stage application under 35 U.S.C. § 371 of International Application No. PCT/US2019/038569, having an International Filing Date of Jun. 21, 2019, which claims priority to U.S. Application Ser. No. 62/688,822, filed on Jun. 22, 2018. The disclosure of the prior application is considered part of (and is incorporated by reference in) the disclosure of this application.

STATEMENT REGARDING FEDERAL FUNDING

This invention was made with government support under DK119167 awarded by the National Institutes of Health. The government has certain rights in the invention.

BACKGROUND

1. Technical Field

This document relates to methods and materials for improving arteriovenous fistula (AVF) maturation and/or maintaining AVF functionality. For example, this document relates to using one or more senolytic agents (e.g., dasatinib, a tocotrienol, quercetin, or a combination thereof) to improve AVF maturation, to maintain AVF functionality, and/or to maintain the patency of an AVF. This document also relates to using one or more senolytic agents (e.g., dasatinib, a tocotrienol, quercetin, or a combination thereof) to maintain functionality and/or patency of a venous graft (e.g., a venous graft used to bypass an arterial occlusion).

2. Background Information

The formation of an AVF abruptly conjoins vascular segments that became separate and distinct early in vascular development. During embryogenesis, subsets of angioblasts in the primitive capillary plexus move apart and differentiate into what will become arteries and veins (Potente et al., Nat. Rev. Mol. Cell Biol., 18:477-494 (2017)). Vascular specialization is driven by signaling species from surrounding tissue and angioblasts themselves, the final structures of arteries and veins also shaped by their respective hemodynamic profiles (Potente et al., Nat. Rev. Mol. Cell Biol., 18:477-494 (2017)). Fully developed arteries are resilient with high intraluminal pressure, pulsatile flow, and low capacitance. Veins, conversely, are flaccid and delicate-walled, with low intraluminal pressure, low and steady flow, and high capacitance. An AVF, in a certain sense, thus reverses the course of vascular development, thereby subjecting veins to the heightened pressures and flows they were never designed to bear, and imposing pathologic shear stress on both vessels. The study of the AVF thus offers insights into vascular behavior when the vasculature is uniquely and severely stressed.

The study of the AVF also is of fundamental clinical importance as an AVF, created in superficial, upper extremity vessels, provides a therapeutic device: namely, a high-flow, accessible, venous segment for hemodialysis for end-stage renal disease (ESRD). Indeed, the AVF, compared with other accesses, is the most favored, promoted as it is by the "Fistula First" initiative (Mehrotra et al., J. Am. Soc. Nephrol., 28:395-397 (2017); Nath et al., Clin. J. Am. Soc. Nephrol., 12:2053-2055 (2017); Riella et al., Nat. Rev. Nephrol., 9:348-357 (2013); Roy-Chaudhury et al., J. Am. Soc. Nephrol., 17:1112-1127 (2006); and Viecelli et al., Semin. Dial., 31:244-257 (2018)).

To support intermittent hemodialysis, the AVF must undergo "maturation." Maturation requires markedly increased blood flow as the artery dilates and both vessels undergo luminal expansion and outward remodeling. Outward remodeling also toughens the vein, allowing it to be repeatedly punctured for dialysis (Nath et al., J. Am. Soc. Nephrol., 27:3508-3510 (2016); Riella et al., Nat. Rev. Nephrol., 9:348-357 (2013); and Roy-Chaudhury et al., J. Am. Soc. Nephrol., 17:1112-1127 (2006)). Additionally, maturation and sustained function require suppression of inward remodeling (neointimal hyperplasia and thrombogenesis) (Nath et al., J. Am. Soc. Nephrol., 27:3508-3510 (2016); Riella et al., Nat. Rev. Nephrol., 9:348-357 (2013); and Roy-Chaudhury et al., J. Am. Soc. Nephrol., 17:1112-1127 (2006)).

Clinical AVF outcomes, however, are truly grim: 50% of created AVFs may never mature; 30% require instrumentation to mature; and the median survival for AVFs is 7.5 months, which increases to 62 months when primary AVF failure is excluded (Lok et al., Clin. J. Am. Soc. Nephrol., 8:810-818 (2013)). Even after maturation, 15% will be nonfunctional after 1 year, and 25% after 2 years (Roy-Chaudhury et al., J. Am. Soc. Nephrol., 17:1112-1127 (2006)). Dysfunction of AVFs and other accesses markedly contributes to morbidity, mortality, and hospitalization rates (~25%) in patients with ESRD, imposing healthcare costs that may exceed $2.5 billion/year (USRDS 2009 Annual Data Report: Atlas of Chronic Kidney Disease and End-Stage Renal Disease in the United States. Bethesda (MD): U.S. Renal Data System, National Institutes of Health, National Institute of Diabetes and Digestive and Kidney Diseases, 2009).

There is no specific therapy that promotes maturation and functionality of human AVFs. Of all the unmet needs in ESRD, this is among the most pressing (Nath et al., Clin. J. Am. Soc. Nephrol., 12:2053-2055 (2017); Roy-Chaudhury et al., J. Am. Soc. Nephrol., 17:1112-1127 (2006); and Viecelli et al., Semin. Dial., 31:244-257 (2018)). Strategies targeted to this need largely rely on acceptable rodent AVF models to understand the basis for AVF failure. Studies in rodent and human AVFs have revealed an induction of potentially vasculopathic species, but, thus far, the underlying mechanism that underpins vasculopathic responses remains elusive.

SUMMARY

This document provides methods and materials for improving AVF maturation and/or maintaining AVF functionality. For example, this document provides methods and materials for using one or more senolytic agents (e.g., dasatinib, a tocotrienol, quercetin, or a combination thereof) to improve AVF maturation, to maintain AVF functionality, and/or to maintain the patency of an AVF. This document also provides methods and materials for using one or more senolytic agents (e.g., dasatinib, a tocotrienol, quercetin, or a combination thereof) to maintain functionality and/or patency of a venous graft (e.g., a venous graft used to bypass an arterial occlusion).

As described herein, administering a composition comprising one or more senolytic agents to a mammal (e.g., a human) having a surgically created AVF can promote maturation of the AVF such that it can be used as an effective hemodialysis vascular access. In some cases, a composition comprising one or more senolytic agents can be administered locally to an AVF (e.g., a surgically created AVF) to promote maturation of the AVF. Having the ability to promote maturation of an AVF as described herein can allow clinicians and patients to use effective hemodialysis vascular access points that would not otherwise be available. Having the ability to promote maturation of an AVF as described herein also can allow clinicians and patients to achieve efficient hemodialysis that would not otherwise be available.

As also described herein, administering a composition comprising one or more senolytic agents to a mammal (e.g., a human) having a surgically created AVF can maintain functionality and/or patency of the AVF such that it can continue to be used as an effective hemodialysis vascular access. In some cases, a composition comprising one or more senolytic agents can be administered locally to an AVF (e.g., a surgically created AVF) to maintain functionality and/or patency of the AVF. Having the ability to maintain functionality and/or patency of an AVF as described herein can allow clinicians and patients to use effective hemodialysis vascular access points for extended periods of time.

In addition, as described herein, administering a composition comprising one or more senolytic agents to a mammal (e.g., a human) having a venous graft (e.g., a venous graft attached to an artery such as a venous graft for bypassing an occluded artery) can maintain functionality and/or patency of the venous graft. In some cases, a composition comprising one or more senolytic agents can be administered locally to a venous graft to maintain functionality and/or patency of the venous graft. Having the ability to maintain functionality and/or patency of a venous graft as described herein can allow clinicians and patients to use functional venous grafts for extended periods of time.

In general, one aspect of this document features a method for promoting arteriovenous fistula maturation within a mammal. The method comprises (or consists essentially of or consist of) administering a composition comprising a senolytic agent to the mammal, wherein the arteriovenous fistula matures into an effective vascular access point for hemodialysis. The mammal can be a human. The composition can comprise dasatinib, a tocotrienol, quercetin, or a combination thereof. The composition can comprise dasatinib and quercetin. The composition can comprise a tocotrienol and quercetin. The administration can comprise a local administration to the arteriovenous fistula. In some cases, the senolytic agent can be the sole active ingredient of the composition to promote arteriovenous fistula maturation within the mammal.

In another aspect, this document features a method for maintaining functionality of an arteriovenous fistula within a mammal. The method comprises (or consists essentially of or consist of) administering a composition comprising a senolytic agent to the mammal, wherein the arteriovenous fistula remains functional as effective vascular access point for hemodialysis following the administering step. The mammal can be a human. The composition can comprise dasatinib, a tocotrienol, quercetin, or a combination thereof. The composition can comprise dasatinib and quercetin. The composition can comprise a tocotrienol and quercetin. The administration can comprise a local administration to the arteriovenous fistula. In some cases, the senolytic agent can be the sole active ingredient of the composition to maintain functionality of the arteriovenous fistula within the mammal.

In another aspect, this document features a method for maintaining patency of an arteriovenous fistula within a mammal. The method comprises (or consists essentially of or consist of) administering a composition comprising a senolytic agent to the mammal, wherein the arteriovenous fistula remains open following the administering step. The mammal can be a human. The composition can comprise dasatinib, a tocotrienol, quercetin, or a combination thereof. The composition can comprise dasatinib and quercetin. The composition can comprise a tocotrienol and quercetin. The administration can comprise a local administration to the arteriovenous fistula. In some cases, the senolytic agent can be the sole active ingredient of the composition to maintain patency of the arteriovenous fistula within the mammal.

In another aspect, this document features a method for maintaining functionality of venous graft within a mammal. The method comprises (or consists essentially of or consist of) administering a composition comprising a senolytic agent to the mammal, wherein the venous graft remains functional as effective graft following the administering step. The mammal can be a human. The composition can comprise dasatinib, a tocotrienol, quercetin, or a combination thereof. The composition can comprise dasatinib and quercetin. The composition can comprise a tocotrienol and quercetin. The administration can comprise a local administration to the venous graft. The venous graft can be a venous graft that bypasses an occluded artery within the mammal. The venous graft can be attached to a coronary artery. The mammal can have an ischemic heart disease. The venous graft can be attached to a carotid artery. The mammal can have a cerebrovascular disease. The venous graft can be attached to a femoral or popliteal artery. The mammal can have a peripheral arterial disease. The venous graft can be attached to a renal artery. The mammal can have a renovascular disease. The venous graft can be attached to a mesenteric artery. The mammal can have a mesenteric arterial disease or abdominal angina. In some cases, the senolytic agent can be the sole active ingredient of the composition to maintain functionality of the venous graft within the mammal.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DETAILED DESCRIPTION

Figure 1A:
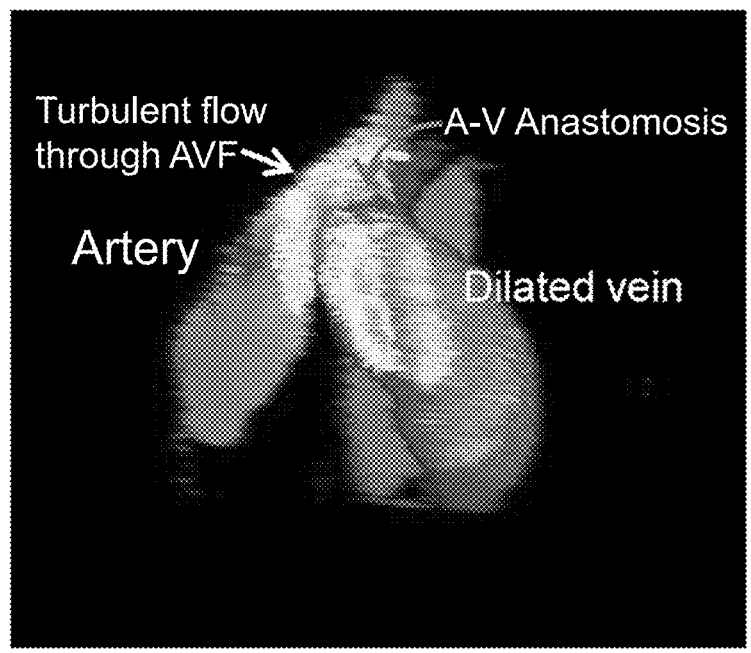
FIGS. 1A-E. Stressors in the vein in the AVF-CKD model. A. 3D Color Doppler ultrasound of the AVF in the AVF-CKD group. Red and blue colors indicate cranial and caudal blood flow in the AVF artery and vein, respectively. Oscillatory flow at the anastomosis is revealed by the yellow mosaic pattern, and a mixture of caudal (blue) and cranial-directed (red) flow is seen in the dilated AVF vein. B. Western analysis of PCNA and β-catenin expression in sham veins and in the vein of the AVF-CKD model, and normalized expression at one week (*P<0.05). C. IL-1α, IL-6, and MCP-1 mRNA expression in sham veins and in the vein of the AVF-CKD model at one week; n=9 and n=10 for sham and AVF-CKD groups, respectively, *P<0.01. D. $pO_2$ in blood from sham veins and from the vein of the AVF-CKD model after AVF/sham surgery; n=6 in each group, *P<0.05. E. Heat map of RNA-seq analysis of sham veins and the vein of the AVF-CKD model at one week. The map is comprised of 2,427 genes with a false discovery rate below 0.05 and an absolute log 2 fold change of 2 or greater. Green to red coloring was calculated from each sample's RPKM value for each gene and then transformed to z-scores. Significant transcriptomic landscape differences distinguish each group; unsupervised clustering with the MeV software perfectly separated the sham vein samples from the AVF-CKD samples.

This document provides methods and materials for improving AVF maturation and/or maintaining AVF functionality. For example, this document provides methods and materials for using one or more senolytic agents (e.g., dasatinib, a tocotrienol, quercetin, or a combination thereof) to improve AVF maturation, to maintain AVF functionality, and/or to maintain the patency of an AVF within a mammal (e.g., a human). This document also provides methods and materials for using one or more senolytic agents (e.g., dasatinib, a tocotrienol, quercetin, or a combination thereof) to maintain functionality and/or patency of a venous graft (e.g., a venous graft used to bypass an arterial occlusion) within a mammal (e.g., a human).

Examples of mammals that can be treated as described herein include, without limitation, humans, monkeys, dogs, cats, cows, horses, pigs, rats, and mice. In some cases, the mammal can be a mammal (e.g., a human) that requires hemodialysis and has an arteriovenous fistula. In some cases, the mammal can be a mammal (e.g., a human) that has a venous graft.

Arteries are elastic and resilient with high intraluminal pressure, pulsatile flow, and low capacitance. Veins are flaccid and delicate-walled, lack tensile strength, and are characterized by low intraluminal pressure, low and steady flow, and high capacitance. Venous blood contains oxygen at a relatively low partial pressure of oxygen, whereas the partial pressure of oxygen in arterial blood is markedly higher. Connecting a vein to the side of an artery, as is done when a dialysis AVF is created, subjects the vein to greatly increased blood pressures, blood flow rates, and blood oxygenation, all of which the vein was never designed to bear. As described herein, this profound hemodynamic and oxygenation stress can cause accelerated senescence of the vein, and, ultimately, failure of the vein to mature and/or AVF failure. The methods and material provided herein can be used to promote maturation of an AVF within a mammal and/or to maintain the functionality and/or patency of an AVF within a mammal. For example, a composition containing one or more senolytic agents can be administered to a mammal (e.g., a human) having an AVF to promote maturation of the AVF within the mammal and/or to maintain the functionality and/or patency of the AVF within the mammal.

Veins also are anastomosed to arteries when there is an occlusion in the artery that impedes blood flow to a relevant organ or tissue. The proximal end of this venous graft can be anastomosed "upstream" of the arterial occlusion, and the distal end of this venous graft can be anastomosed "downstream" of the arterial occlusion. In this way, the arterial occlusion can be entirely bypassed by the venous graft. These venous grafts can be subjected to the markedly increased blood pressures, blood flow, and blood oxygenation of the arterial circulation. Such hemodynamic and oxygenation stress can cause senescence in these venous grafts used to bypass diseased arteries, causing these venous grafts to fail. Venous grafts are widely used to bypass arterial occlusions in diseased arteries as broadly occurs in atherosclerotic cardiovascular disease such cardiovascular disease, which is a leading cause of death in the United States and other developed countries. The methods and material provided herein can be used to maintain the functionality and/or patency of a venous graft within a mammal. For example, a composition containing one or more senolytic agents can be administered to a mammal (e.g., a human) having a venous graft to maintain the functionality and/or patency of the venous graft within the mammal.

Examples of venous grafts used to bypass an occluded artery that can be treated with a composition containing one or more senolytic agents as described herein to maintain functionality and/or patency of the venous graft include, without limitation, venous grafts used in coronary arteries in mammals with, for example, ischemic heart disease, venous grafts used in carotid arteries in mammals with, for example, cerebrovascular disease, venous grafts used in femoral or popliteal arteries in mammals with, for example, peripheral arterial disease, venous grafts used in renal arteries in mammals with, for example, renovascular disease, and venous grafts used in mesenteric arteries in mammals with, for example, mesenteric arterial disease (e.g., abdominal angina).

Examples of senolytic agents that can be used as described herein include, without limitation, dasatinib, a tocotrienol, quercetin, fisetin, luteolin, navitoclax, A1331852 (CAS Number 1430844-80-6; 6-[8-[(2-benzothiazolylamino)carbonyl]-3,4-dihydro-2(1H)-isoquinolinyl]-3-[5-methyl-1-(tricyclo[3.3.1.13.7]dec-1-ylmethyl)-1H-pyrazol-4-yl]-2-pyridinecarboxylic acid), A1155463 (CAS Number 1235034-55-5; 2-[8-[[(2-Benzothiazolylamino)carbonyl]-3,4-dihydro-2(1H)-isoquinolinyl]-5-[3-[4-[3-(dimethylamino)-1-propyn-1-yl]-2-fluorophenoxy]propyl]-4-thiazolecarboxylic acid), 17-AAG (Tanespimycin), geldanamycin, piperlongumine, 17-DMAG (Alvespimycin), and panobinostat.

A composition for treating an AVF and/or venous graft as described herein can include one senolytic agent or more than one senolytic agent (e.g., two, three, four, five, or more senolytic agents). For example, a composition can be designed to include dasatinib and quercetin and can be used promote AVF maturation in a mammal. In some cases, two, three, four, or five different senolytic agents can be administered in combination or sequentially to a mammal with an AVF and/or a venous graft.

In some cases, a senolytic agent can be chemically converted from its free base form to a pharmaceutically acceptable salt by reacting the free base with an equivalent amount of an acid that forms a non-toxic salt, which can be used to treat an AVF and/or venous graft as described herein or to form a composition that can be used to treat an AVF and/or venous graft as described herein. Such acids can be either inorganic or organic including, without limitation, hydrochloric acid, hydrobromic acid, fumaric acid, maleic acid, succinic acid, sulfuric acid, phosphoric acid, tartaric acid, acetic acid, citric acid, and oxalic acid. In some cases, a senolytic agent (or a pharmaceutically acceptable salt thereof) provided herein can be administered to a mammal by itself or in combination with a carrier. Such carriers include, without limitation, sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, alcohol, saline, and buffered solutions. In some cases, preservatives, flavorings, and other additives such as, for example, antimicrobials, anti-oxidants, chelating agents, inert gases, and the like can be present. It will be appreciated that a senolytic agent (or a pharmaceutically acceptable salt thereof) provided herein that is to be administered to a mammal can contain zero, one, or more than one pharmaceutically acceptable carriers.

A senolytic agent or a composition containing one or more senolytic agents provided herein can be administered to any part of a mammal's body. For example, a senolytic agent or a composition containing one or more senolytic agents provided herein can be administered directly to an AVF or venous graft of a mammal. In some cases, a senolytic agent or a composition containing one or more senolytic agents provided herein can be administered via an adventitial administration. In some cases, a senolytic agent or a composition containing one or more senolytic agents provided herein can be administered intravenously, subcutaneously, intraperitoneal, or orally.

When treating a mammal (e.g., a human) having an AVF, an effective amount of a senolytic agent or a composition containing one or more senolytic agents provided herein can be any amount that, when administered to the mammal having an AVF, promotes AVF maturation and/or maintains the functionality and/or patency of the AVF as described herein without inducing significant toxicity in the mammal. When treating a mammal (e.g., a human) having a venous graft, an effective amount of a senolytic agent or a composition containing one or more senolytic agents provided herein can be any amount that, when administered to the mammal having a venous graft, maintains the functionality and/or patency of the venous graft as described herein without inducing significant toxicity in the mammal. Such amounts can be determined using the methods and materials provided herein. Some compounds may have a relatively broad concentration range that is effective, while others may have a relatively narrow effective concentration range. In addition, the effective amount can vary depending upon the specific mammal or the specific condition of an AVF or venous graft. Such effective amounts can be determined for individual compounds using available or ascertainable information involving equilibrium dissociation constants, mammal toxicity concentrations, and bioavailability. For example, non-toxic compounds typically can be directly or indirectly administered to a mammal in any amount that induces a desired result in that mammal.

Using the information provided herein, such effective amounts also can be determined in vitro or in vivo. For example, a mammal (e.g., a human) can receive direct administration of a senolytic agent provided herein in an amount to achieve a desired result. If the patient fails to respond, then the amount can be increased by, for example, two fold. After receiving this higher concentration, the patient can be monitored for both responsiveness to the treatment and toxicity symptoms, as well as blood levels of the drug, and adjustments made accordingly.

Various factors can influence the actual effective amount used for a particular application. For example, the frequency of administration, duration of treatment, rate of metabolism of the senolytic agent, combination of other compounds, and site of administration may require an increase or decrease in the actual effective amount administered.

The frequency of administration can be any frequency that induces a desired result within a mammal without producing significant toxicity to the mammal. For example, the frequency of administration can be from about twice a day to about once a month, or more specifically, from about once a week to about once a month (e.g., orally or topically, for example, as a cream, ointment, emulsion, or suspension over the site of the AVF, or by injection into the fistula or systemically). In addition, the frequency of administration can remain constant or can be variable during the duration of treatment. As with the effective amount, various factors can influence the actual frequency of administration used for a particular application. For example, the effective amount, duration of treatment, rate of metabolism of the senolytic agent, combination of other compounds, and site of administration may require an increase or decrease in administration frequency.

An effective duration for administration of a compound provided herein can be any duration that induces a desired result within a mammal without producing significant toxicity to the mammal. Thus, the effective duration can vary from several days to several weeks, months, or years. In general, the effective duration for promoting AVF maturation into an effective hemodialysis vascular access point in a mammal can range in duration from one day to one, two, three, four, or five months. In some cases, the effective duration for maintaining the functionality and/or patency of an AVF in a mammal can range in duration from one day, one week, or one month to one, two, three, four, five, or more years. In some cases, the effective duration for maintaining the functionality and/or patency of a venous graft in a mammal can range in duration from one day, one week, or one month to one, two, three, four, five, or more years. Multiple factors can influence the actual effective duration used for a particular treatment regimen. For example, an effective duration can vary with the frequency of compound administration, effective compound amount, combination of multiple compounds, and site of administration.

The level of toxicity, if any, can be determined by assessing a mammal's clinical signs and symptoms before and after administering a known amount of a particular composition. It is noted that the effective amount of a particular composition administered to a mammal can be adjusted according to a desired outcome as well as the mammal's response and level of toxicity.

The invention will be further described in the following examples, which do not limit the scope of the invention described in the claims.

EXAMPLES

Example 1—Dialysis Fistula Exhibits a Senescence Phenotype in Mice

Methods and Materials

The AVF-CKD model was created in male C57BL/6J mice as described elsewhere in which an AVF/sham AVF was created in mice in which CKD/sham CKD was previously imposed (Kang et al., Am. J. Physiol. Renal Physiol., 310: F466-476 (2016)). At one week after AVF/sham AVF, the vasculature was harvested for assorted analyses and assessment of senescence-associated beta galactosidase (SA-β-Gal) activity. At two weeks, ultrasound studies were performed. In selected studies, $pO_2$ was measured by an i-Stat analyzer (Abbott Point of Care, Princeton, NJ) in venous blood samples drawn immediately after AVF/sham AVF. In other studies, mice with AVF-CKD were treated with the senolytic agent combination (dasatinib, 5 mg/kg, and quercetin, 50 mg/kg) or vehicle via gavage on days 4 and 5 after AVF creation (Schafer et al., Nat. Commun., 8:14532 (2017); and Zhu et al., Aging Cell, 14:644-658 (2015)), and p16Ink4a protein expression was assessed at 7 days.

Vascular Ultrasound

Sonography was performed using a high-resolution imaging (Vevo2100 with a MS400 30-MHz transducer, Vevo3100 with a MX400 38-MHz transducer, FUJIFILM VisualSonics Inc., Toronto, Canada) (Wang et al., Arterioscler. Thromb. Vasc. Biol., 35:1401-1412 (2015)). Blood flow dynamics was three-dimensionally (3D) reconstructed from a serial 2D color Doppler at 32-μm intervals (Wang et al., Arterioscler. Thromb. Vasc. Biol., 35:1401-1412 (2015)).

Gene Expression by RNA-Seq

Total RNA was extracted as described elsewhere (Kang et al., Am. J. Physiol. Renal Physiol., 310:F466-476 (2016)). RNA-Sequencing samples were processed through Mayo Clinic's MAP-RSeq V2 software (Kalari et al., BMC Bioinformatics, 15:224 (2014)). This was a comprehensive RNA-Sequencing workflow for Illumina paired end reads. The reference genome and transcriptome used was Ensembl's *Mus musculus* GRCm38.79. Quality control metrics from RSeqQC were evaluated to insure that raw expression values from each sample were reliable and could be collectively used for differential expression analysis (Wang et al., Bioinformatics, 28:2184-2185 (2012)). Genes with an average of 25 or more reads were kept for performing differential expression analysis. The R package (edgeR) was used to identify which genes were statistically differentially expressed from the group comparisons (Robinson et al., Bioinformatics, 26:139-140 (2010)). For each comparison, unsupervised clustering was implemented with the MeV (Howe et al., Bioinformatics, 27:3209-3210 (2011)) application on genes with a false discovery rate below 0.05 and with an absolute log 2 fold change of 2 or greater. MeV was additionally used to visualize these findings through heat maps.

mRNA and microRNA Expression mRNA expression was performed as described (Kang et al., Am. J. Physiol. Renal Physiol., 310:F466-476 (2016); and Kang et al., Am. J. Physiol. Heart Circ. Physiol., 308:H1402-1413 (2015)) using quantitative real-time RT-PCR. microRNA (miRNA) expression was determined in total RNA using a mirVana miRNA isolation kit (Thermo Fisher Scientific, Waltham, MA). Quantitation was performed using Taqman miRNA assays (Applied Biosystems, Foster City, CA).

Western Blot Analysis

Vascular protein extracts were prepared as described elsewhere (Kang et al., Am. J. Physiol. Renal Physiol., 310:F466-476 (2016)). Proteins were separated on TGX Stain-Free gels (BioRad, Hercules, CA), visualized by UV light-activation, and transferred to PVDF membranes. Primary antibodies included: p16Ink4a, p21Cip1 (Abcam, Cambridge, MA), p53 (R & D systems. Minneapolis, MN), PCNA (Cell Signaling Technology, Danvers, MA), and β-catenin (BD Biosciences, Franklin Lakes, NJ). Densitometric quantitation of protein expression was normalized to total protein visualized on the PVDF membranes (Gel Doc XR+ imager, BioRad).

SA-β-Gal Activity

This was quantified using a fluorometric assay kit (Enzo Life Sciences, Farmingdale, NY). Staining for SA-β-Gal activity in frozen sections was performed as described elsewhere (Ogrodnik et al., Nat. Commun., 8:15691 (2017)).

Statistics

Data were expressed as means±SE and considered statistically significant for P<0.05. The Student's t-test was used for parametric data and the Mann-Whitney U-test was employed for nonparametric data.

Results

The AVF Exhibits Diverse Stressors and Altered Gene Expression

Figure 1B:
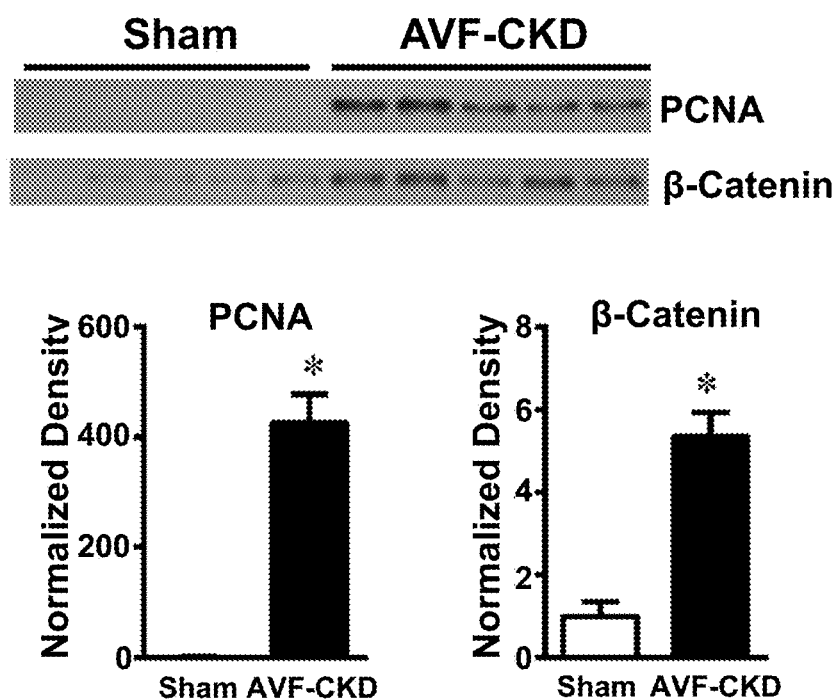
Figure 1C:
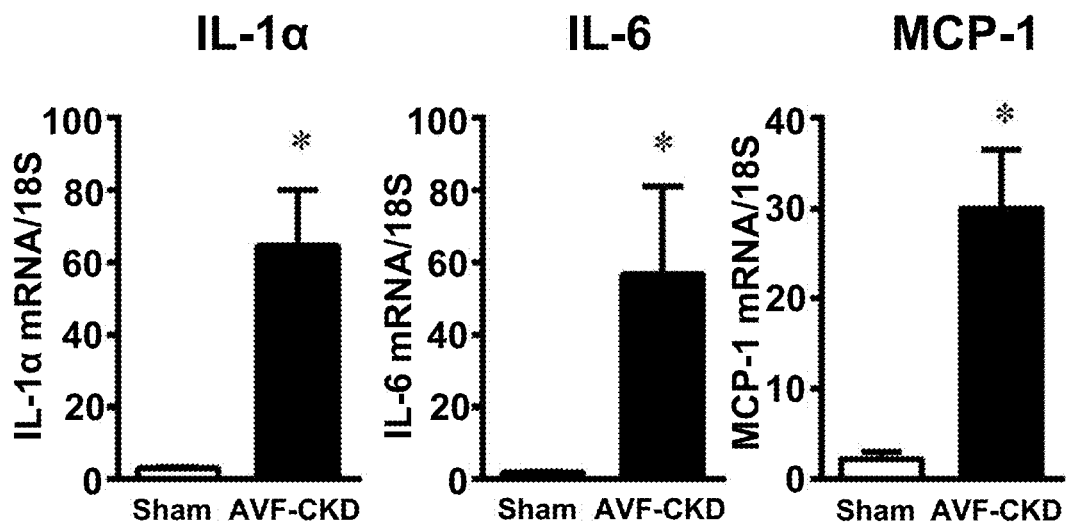
Figure 1D:
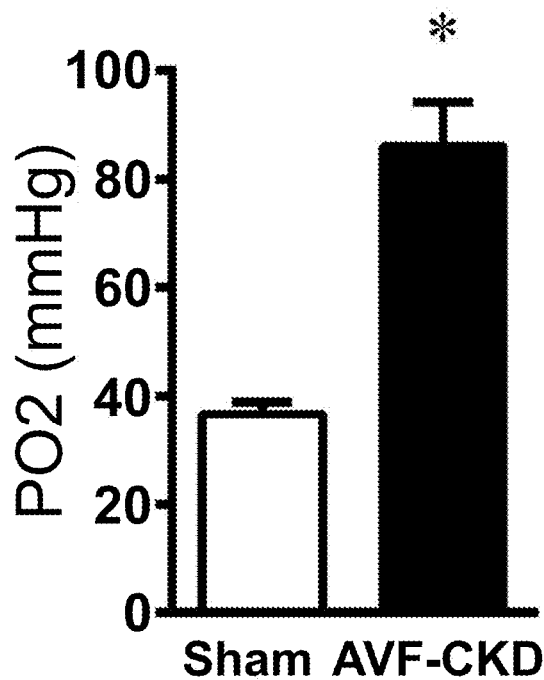

As stress induces vasculopathic responses, whether relevant forms of stress exist in the vein of the AVF was examined. 3D Doppler ultrasound demonstrated the presence of pathologic oscillatory shear stress and turbulent flow (FIG. 1A). Mitogenic and inflammatory stress were also present. Compared with the sham group, the vein of AVF-CKD group exhibited markedly upregulated proliferation markers (PCNA), proliferative signaling species (β-catenin) (FIG. 1B), and pro-inflammatory cytokines (FIG. 1C). Whether reoxygenation stress occurred in the AVF also was considered. Intact veins are normally exposed to a low $pO_2$ to which their metabolism is fully geared. AVF creation immediately exposed the vein to a markedly increased $pO_2$, thereby imposing "hypoxia-reoxygenation" stress on the AVF-CKD (FIG. 1D).

Figure 1E:
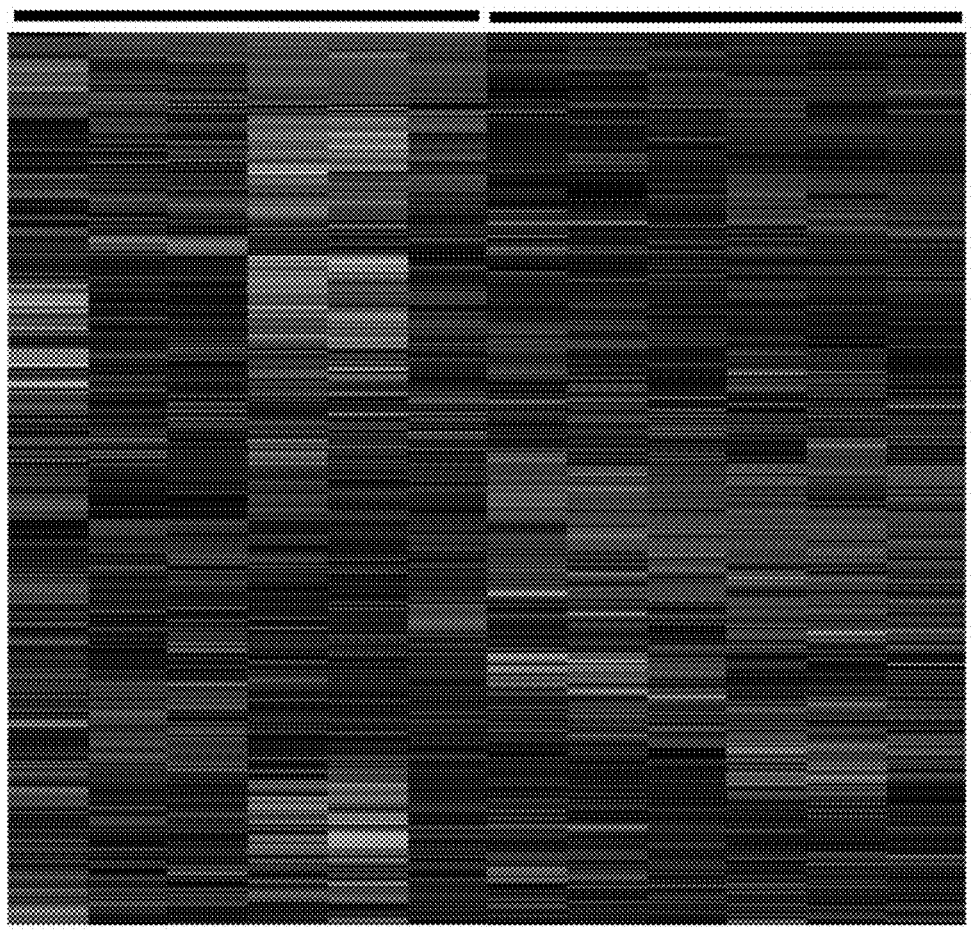
Figure 1E:
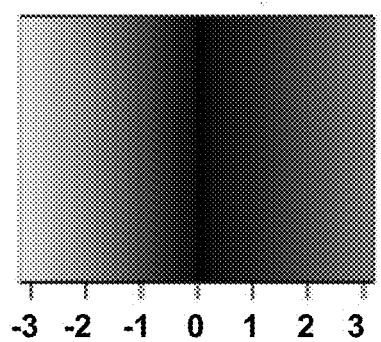

Such stressors were accompanied by altered gene expression in the AVF, as demonstrated by RNA-Seq analyses. Some 20,000 genes were detected, with approximately 10,000 being different in the vein of the AVF-CKD group, including the upregulation of proinflammatory and proliferative genes. The heat map revealed clearly visible transcriptomic landscape differences, thereby distinguishing the veins in the AVF-CKD and Sham groups (FIG. 1E).

AVF Exhibits a Senescence Phenotype

Figure 2A:
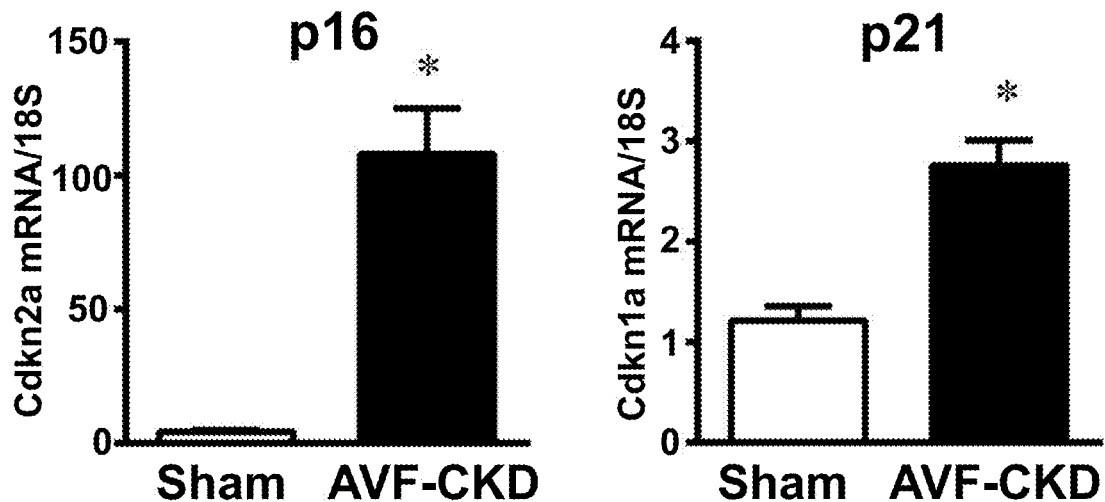
FIGS. 2A-C. Venous senescence markers in the AVF-CKD model. A. Expression of genes encoding for p16Ink4a (Cdkn2a) and p21Cip1 (Cdkn1a) in sham veins and in the vein of the AVF-CKD model, measured by quantitative real-time RT-PCR; n=9 and n=10 for sham and AVF-CKD groups, respectively, *P<0.0001. B. Western analysis of p53, p21Cip1, and p16Ink4a protein expression in sham veins and in the vein of the AVF-CKD model, and normalized expression (*P<0.001). C. miRNA expression of miR-21 (left) and miR-92a (right) in sham veins and in the vein of the AVF-CKD model; n=8 and n=10 for sham and AVF-CKD groups, respectively *P<0.001.
Figure 2B:
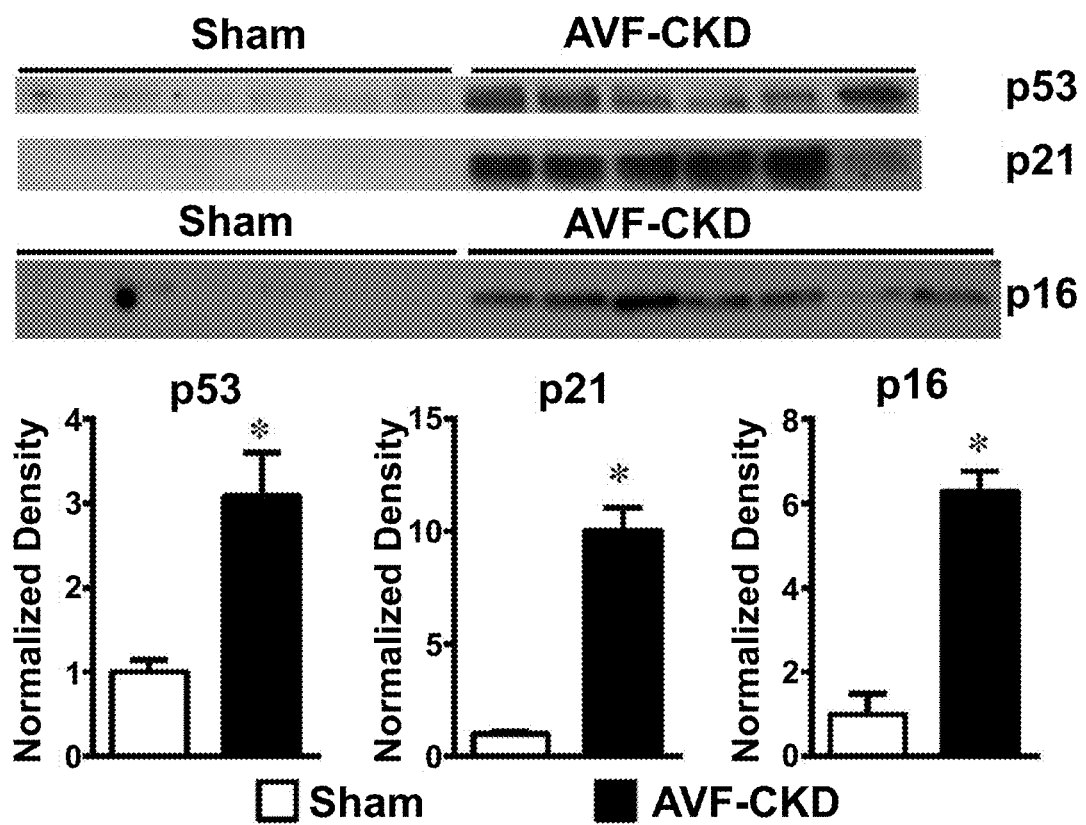
Figure 2C:
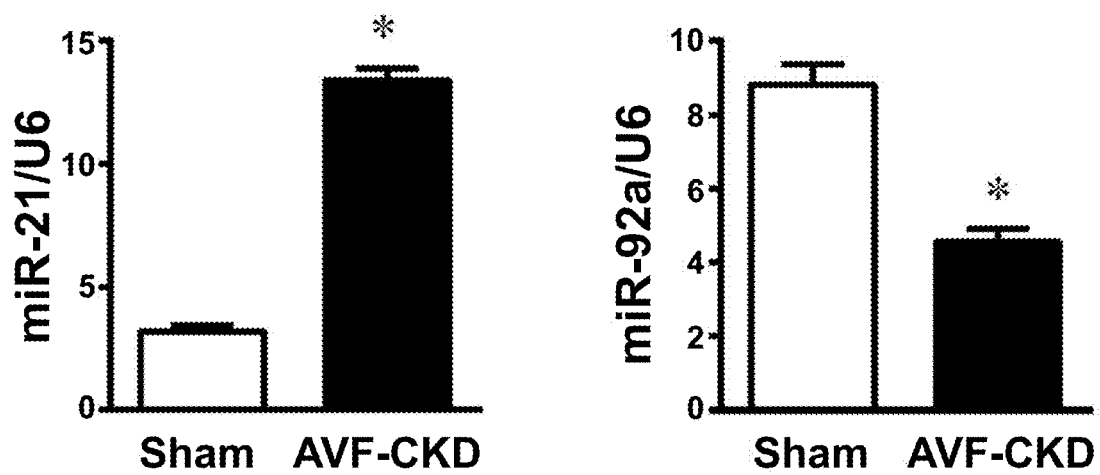

Stress, especially when diverse, may induce premature senescence (Kirkland et al., EBioMedicine, 21:21-28 (2017); Kirkland et al., J. Am. Geriatr. Soc., 65:2297-2301 (2017); and Tchkonia et al., J. Clin. Invest., 123:966-972 (2013)). Whether a senescence phenotype exists in the AVF was examined, beginning with the senescence drivers, p16Ink4a and p21Cip1. Cdkn2a (reflecting mainly p16) and Cdkn1a (reflecting mainly p21) mRNAs were induced in the vein of the AVF. This was accompanied by increased p16Ink4a and p21Cip1 protein expression (FIGS. 2A and 2B). In addition, induction of p53 protein (upstream of p21Cip1 in the senescence pathway) occurred (FIG. 2B). The AVF-CKD vein exhibited changes for certain senescence-associated miRNAs (Olivieri et al., Ageing Res. Rev., 12:1056-1068 (2013); and Hazra et al., Exp. Gerontol., 83:165-170 (2016)). In particular, the AVF-CKD vein exhibited, congruently, increased expression of miR-21 and decreased expression of miR-92a (FIG. 2C).

Figure 3A:
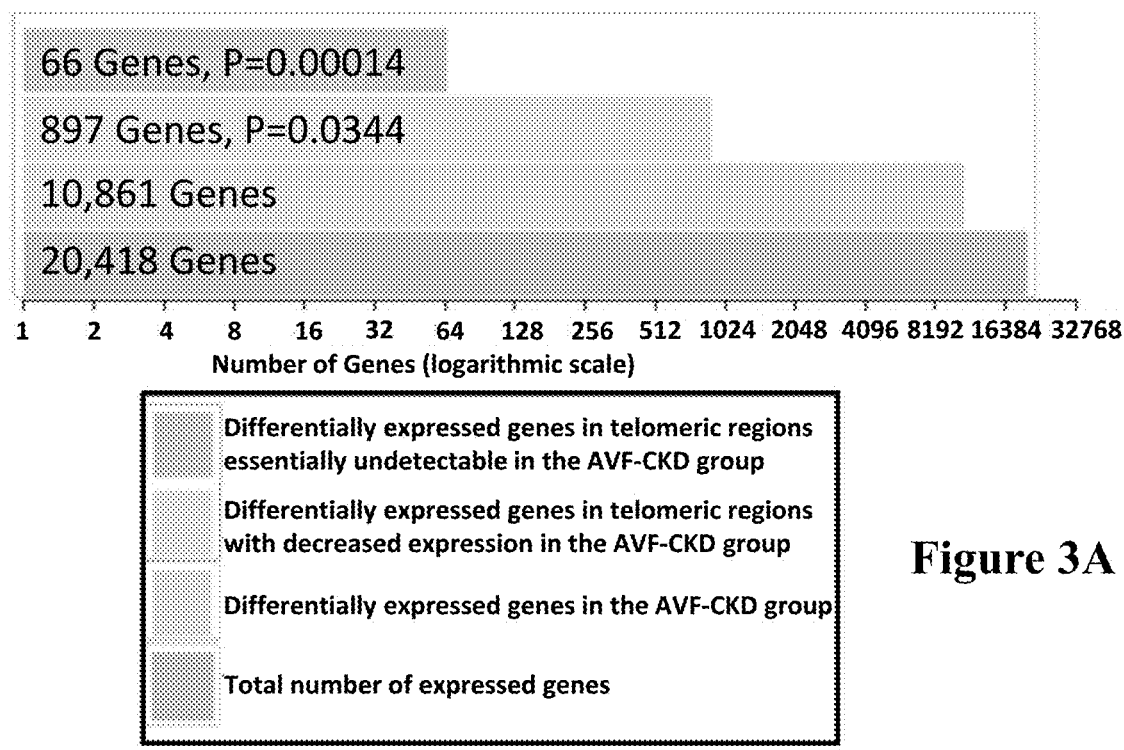
FIGS. 3A-C. Telomere erosion and SA-β-Gal activity/staining in the vein in AVF-CKD. A. Telomere erosion in the AVF-CKD vein as shown by a disproportionate loss of gene expression in the telomeric regions, defined as 10 MBs from the start or end of each autosomal chromosome. Differentially expressed genes were defined by having a false discovery rate equal to or lower than 0.05 when comparing the AVF-CKD group to the sham group. A total of 897 genes in the telomeric regions have decreased expression with a log 2 fold change less than 0, 66 of which have a log 2 fold change less than −4. B. SA-β-Gal activity in sham vein and the vein of the AVF-CKD model at one week; n=5 in each group, *P<0.0001. C. SA-β-Gal activity in frozen sections from sham vein and the vein of the AVF-CKD model at one week. Cells exhibiting increased SA-β-Gal activity exhibit the blue color. The sham group (left) shows no staining, whereas the AVF-CKD model shows blue staining in the endothelium and media.
Figure 3B:
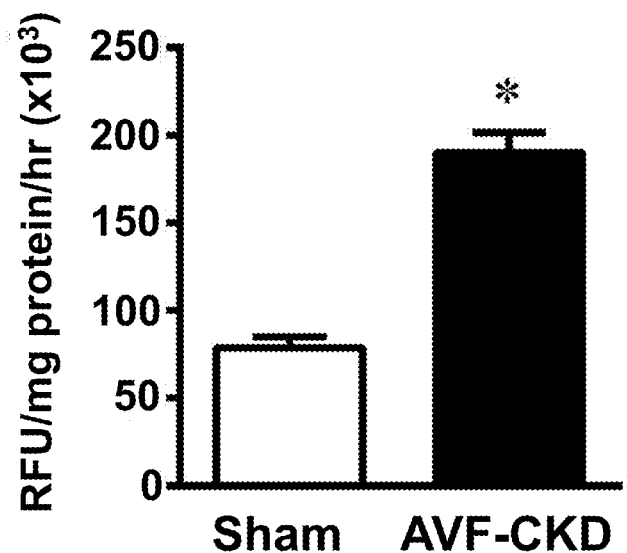
Figure 3C:
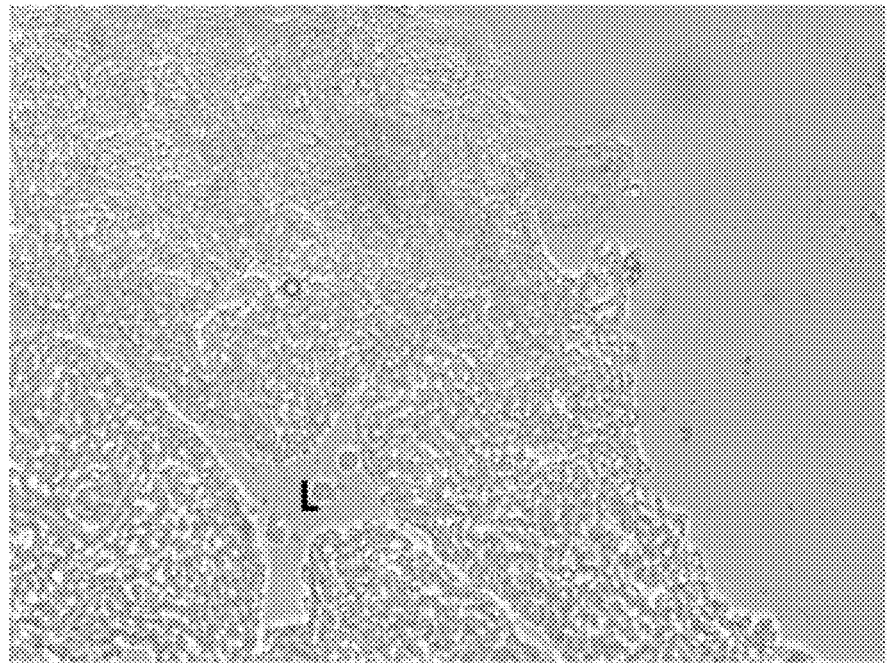
Figure 3C:
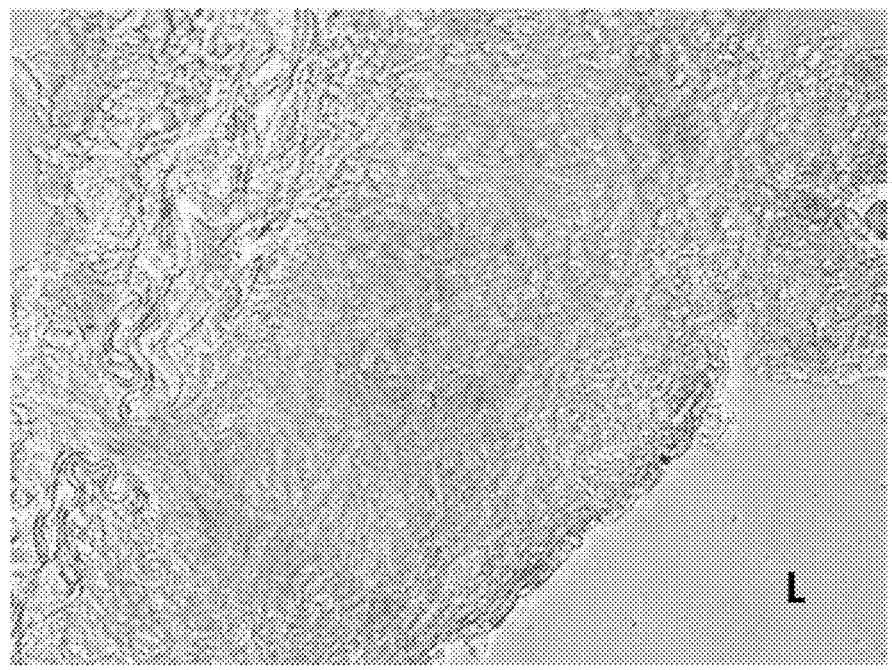

Additional RNA-Seq analyses focused on telomeric regions. Compared with the Sham group, the vein in the AVF-CKD group showed some 900 genes with significantly decreased expression and 66 genes that were essentially undetectable (FIG. 3A). Telomere erosion, a senescence hallmark, thus existed in the vein in the AVF-CKD group. Also present at one week was increased SA-β-Gal activity (FIG. 3B). Studies at one week revealed increased SA-β-Gal (blue) staining in the vein in the AVF-CKD group, with focal cellular staining in the endothelium and tunica media; the control vein was devoid of blue staining (FIG. 3C).

Figure 4A:
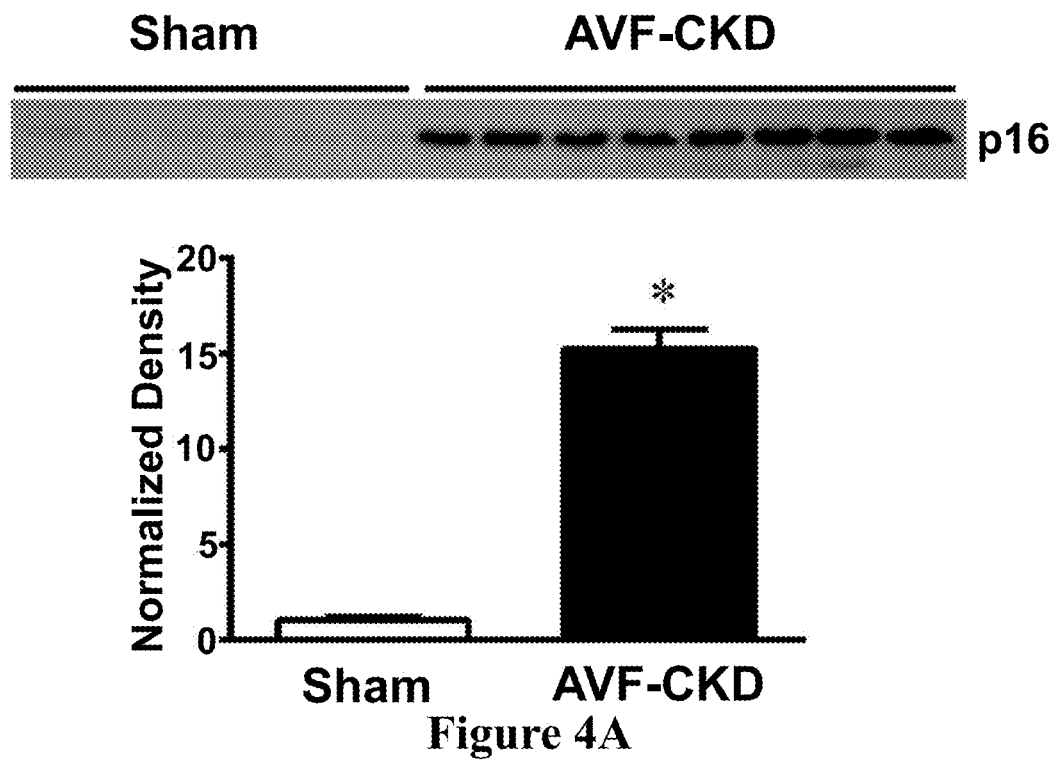
FIGS. 4A-C. p16Ink4a expression in arteries in AVF-CKD, in AVF without CKD, and in the vein in AVF-CKD following administration of senolytics. p16Ink4a protein expression at one week in sham arteries and the artery of the AVF-CKD model (A), in sham veins and the vein of the AVF in mice with normal kidneys (B), and in the vein of the AVF-CKD model administered either vehicle or dasatinib and quercetin (D/Q, C). Normalized expression is below each Western blot. *P<0.001 for A and B, and *P<0.05 for C.
Figure 4B:
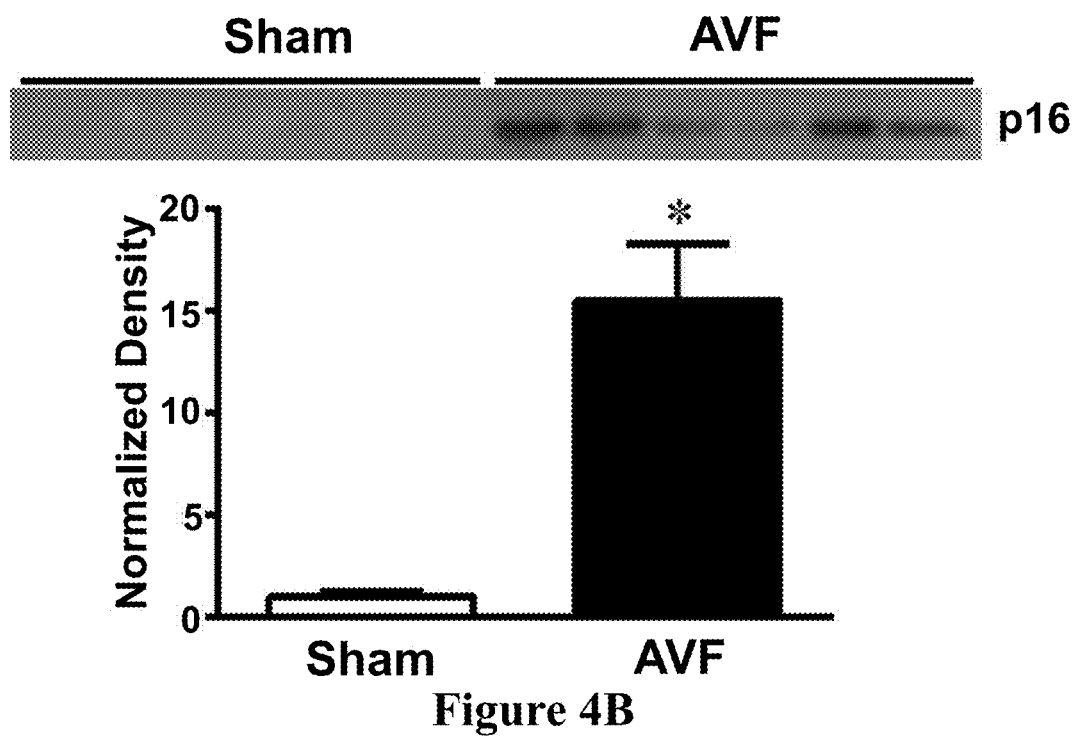
Figure 4C:
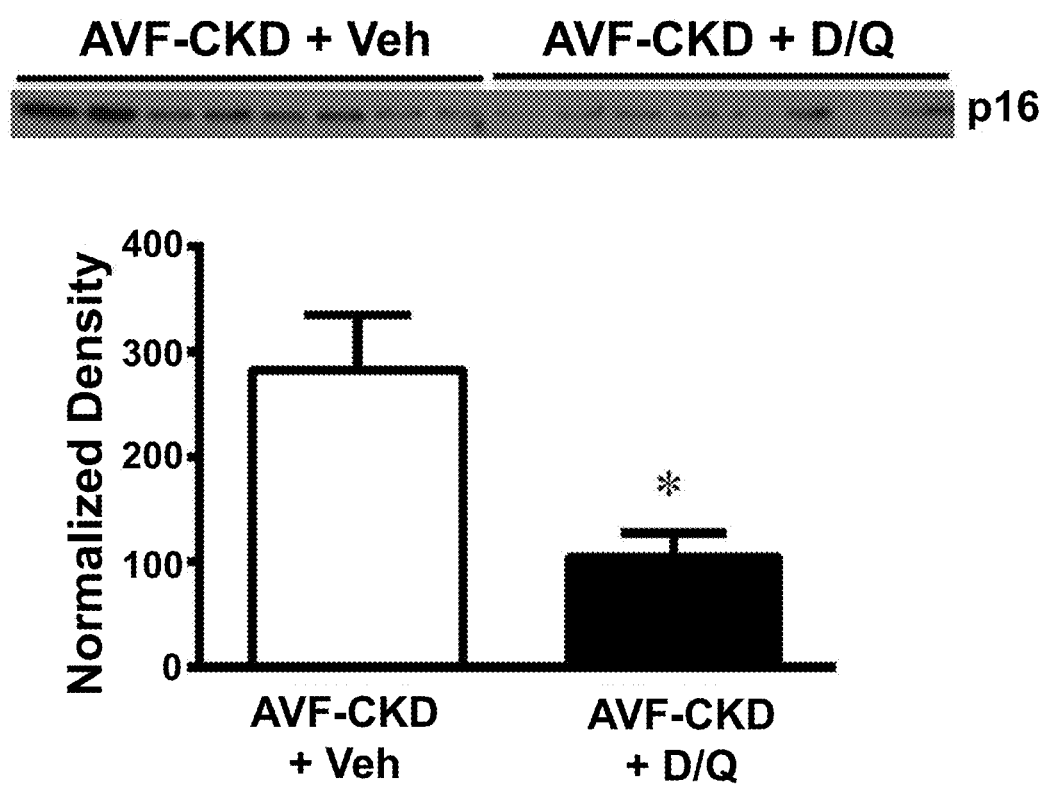

Senescence changes also occurred in the AVF artery as revealed by striking p16Ink4a induction in the artery of the AVF-CKD group (FIG. 4A). The AVF itself, in presence of normal kidney function, evinced p16Ink4a upregulation (FIG. 4B). Finally, the short-term effect of senolytics (dasatinib and quercetin) was examined. Dasatinib and quercetin significantly decreased expression of p16Ink4a at 1 week in the vein in the AVF-CKD group (FIG. 4C).

These results demonstrate that senolytic agents (e.g., locally applied senolytic agents or senolytic agents administered orally, for example, by gavage) can be used to improve arteriovenous fistula maturation, to improve arteriovenous fistula functionality, and to prevent failure of arteriovenous fistulas. These results also demonstrate that senolytic agents can be used to prevent failure of venous grafts, such as venous grafts used to bypass occluded arteries.

Example 2—Dialysis Fistula Exhibits a Senescence Phenotype in Rats

This Examples describes studies in a rat model of the fistula (AVF-CKD) to determine whether the senescence phenotype could be exhibited in multiple species (see Example 1 for studies using a mouse model of the fistula).

Methods and Materials

Rats were first subjected to subtotal nephrectomy, which creates chronic kidney disease (CKD). The rats were anesthetized with pentobarbital (60 mg/kg, IP), and a midline abdominal incision was performed. The gut was gently retracted, thereby exposing the renal pedicles. The right kidney was surgically removed following ligation of the right pedicle with sterile 6-0 silk suture. The arterial vasculature of the left kidney underwent selective segmental ligation with sterile 6-0 silk suture to achieve the desired degree of infarction. The abdominal wall was sutured. In a similar fashion, a sham surgery was performed consisting of the abdominal incision, retraction of the gut, and closure of the abdominal incision. One week after the subtotal nephrectomy or sham surgery, the rats were subjected to AVF surgery. After anesthesia with pentobarbital (60 mg/kg, IP), the rats were placed on a heated surface to maintain body temperature at 37° C. The femoral vasculature was exposed by an incision along the entire length of the inguinal fold and subsequent retraction of the abdominal musculature medially and the inguinal fat pad laterally. The remainder of the procedure was performed under a dissecting microscope at 30× magnification. Using careful dissection, the femoral artery and vein were freed from surrounding fascia and the femoral nerve. Branching vasculature from the femoral artery and vein was ligated with sterile 6-0 silk suture and divided. The femoral vein was then clamped with a non-traumatic vein clip at the proximal end of its exposure, ligated at the distal end of its exposure, and subsequently transected just proximally to the ligation at a 45 degree angle. Non-traumatic aneurysm clips were then placed on the artery at the most proximal and distal points of the exposure, and a small longitudinal incision was made in the artery where the anastomosis was made using a microsurgical knife. Both vessels were rinsed with heparinized saline, and the transected end of the vein was attached to the opening in the adjacent artery with eight equally-spaced interrupted sutures using 10-0 monofilament nylon suture. All clips were then removed, and arterial flow into the femoral vein confirmed. The inguinal incision was then closed with sterile 6-0 vicryl absorbable suture in two separate layers (muscle and skin), using a continuous pattern for each layer. In a similar fashion, a sham surgery was performed on rats, consisting of the inguinal incision, dissection of the vasculature, clamping of the femoral artery and vein, and closure of the inguinal incision. The rats were then allowed to recover from anesthesia.

Determination of β-galactosidase (SA-β-Gal) activity and expression of p21Cip1 and p16Ink4a was performed as described for the mouse.

Figure 5A:
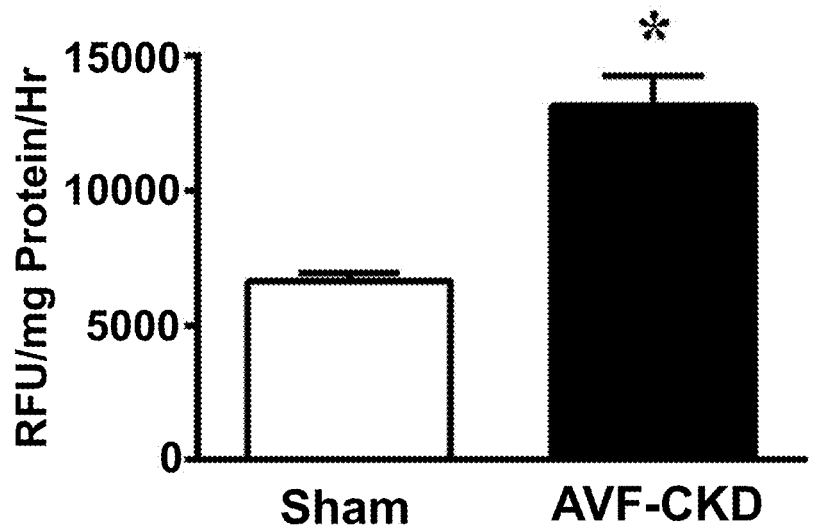
FIGS. 5A-B. Senescence-associated β-Galactosidase (SA-β-Gal) activity in the vein and artery of the rat AVF-CKD model. Activity in veins (A) and arteries (B) from sham and AVF-CKD rats was assessed at 1 week after AVF creation. n=6 and n=7 in the sham and AVF-CKD groups, respectively. *P<0.005.
Figure 5B:
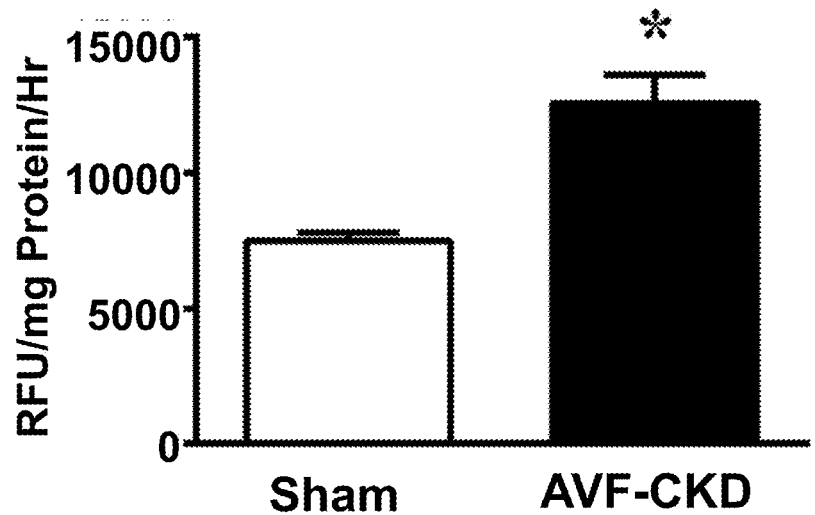
Figure 6A:
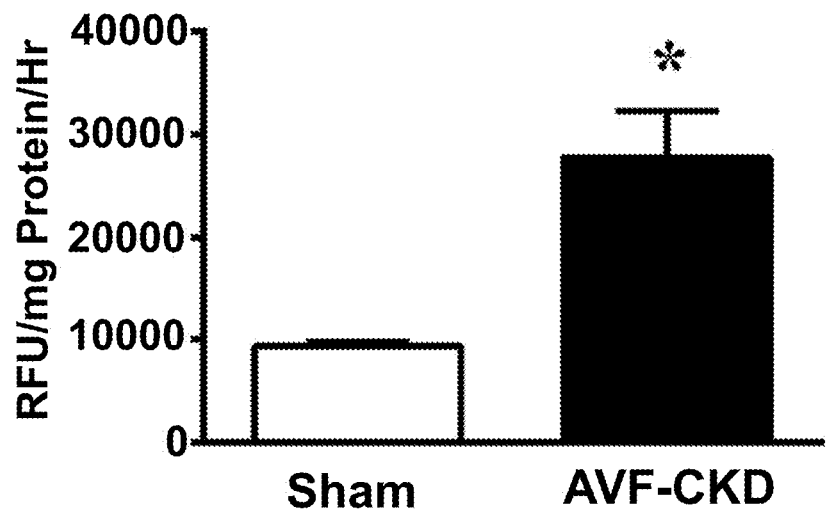
FIGS. 6A-B. Senescence-associated β-Galactosidase (SA-β-Gal) activity in the vein and artery of the rat AVF-CKD model. Activity in veins (A) and arteries (B) from sham and AVF-CKD rats was assessed at 2 weeks after AVF creation. n=5 and n=6 in the sham and AVF-CKD groups, respectively. *P<0.005.
Figure 6B:
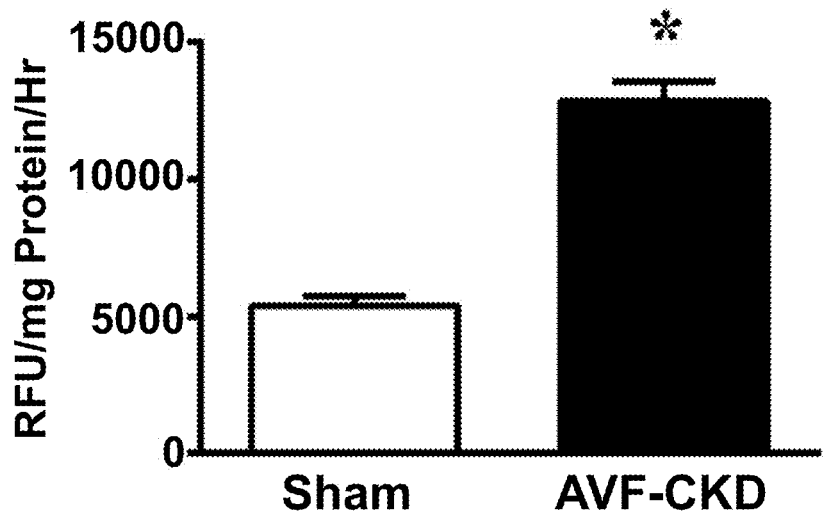

Results

β-galactosidase (SA-β-Gal) activity, a marker of senescence, was significantly increased in the vein and artery in the AVF-CKD model at one week (FIG. 5) and at two weeks (FIG. 6), after the creation of the fistula.

Figure 7A:
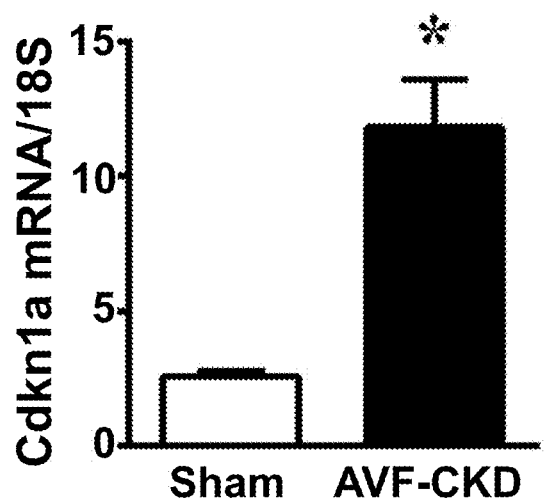
FIGS. 7A-B. p21Cip1 expression in the vein of the rat AVF-CKD model. p21Cip1 mRNA (Cdkn1a, A) and protein (B) expression was assessed in veins from sham and AVF-CKD rats was assessed at 1 week after AVF creation. n=7 and n=9 in the sham and AVF-CKD groups, respectively in A, n=6 and n=7 in the sham and AVF-CKD groups, respectively in B and. *P<0.005.
Figure 7B:
Figure 8:
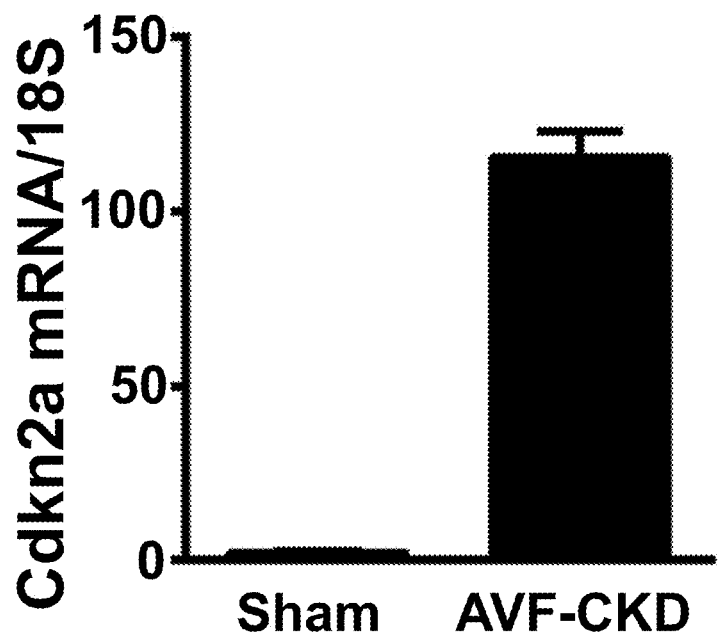
FIG. 8. p16Ink4a expression in the vein of the rat AVF-CKD model. p16Ink4a mRNA (Cdkn2a) expression was assessed in veins from sham and AVF-CKD rats at 1 week after AVF creation. n=7 and n=9 in the sham and AVF-CKD groups, respectively. *P<0.005.

At one week, there was evidence of marked induction of p21Cip1, as reflected both by expression of the p21Cip1 (Cdkn1a) mRNA (FIG. 7A) and the p21 polypeptide (FIG. 7B). There also was an induction of p16Ink4a as reflected by expression of Cdkn2a mRNA (FIG. 8).

These results demonstrate that the senescence phenotype observed in the fistula in mice (see, e.g., Example 1) also is observed in rats.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for maintaining functionality of venous graft within a mammal, wherein said method comprises administering a composition comprising dasatinib, a tocotrienol, quercetin, or a combination thereof to said mammal, wherein said venous graft remains functional as effective graft following said administering step.

2. The method of claim 1, wherein said mammal is a human.

3. The method of claim 1, wherein said composition comprises dasatinib and quercetin.

4. The method of claim 1, wherein said composition comprises a tocotrienol and quercetin.

5. The method of claim 1, wherein said administration comprises a local administration to said venous graft.

6. The method of claim 1, wherein said venous graft bypasses an occluded artery within said mammal.

7. The method of claim 1, wherein said venous graft is attached to a coronary artery.

8. The method of claim 7, wherein said mammal has an ischemic heart disease.

9. The method of claim 1, wherein said venous graft is attached to a carotid artery.

10. The method of claim 9, wherein said mammal has a cerebrovascular disease.

11. The method of claim 1, wherein said venous graft is attached to a femoral or popliteal artery.

12. The method of claim 11, wherein said mammal has a peripheral arterial disease.

13. The method of claim 1, wherein said venous graft is attached to a renal artery.

14. The method of claim 12, wherein said mammal has a renovascular disease.

15. The method of claim 1, wherein said venous graft is attached to a mesenteric artery.

16. The method of claim 15, wherein said mammal has a mesenteric arterial disease or abdominal angina.

* * * * *